(12) United States Patent
Finger et al.

(10) Patent No.: US 12,035,939 B2
(45) Date of Patent: Jul. 16, 2024

(54) PULMONARY NODULE ACCESS DEVICES AND METHODS OF USING THE SAME

(71) Applicant: GYRUS ACMI, INC.

(72) Inventors: Clinton L. Finger, Bellevue, WA (US); Matthew E. Nickeson, Seattle, WA (US); Michael S. Smith, Sammamish, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 223 days.

(21) Appl. No.: 17/466,170

(22) Filed: Sep. 3, 2021

(65) Prior Publication Data
US 2022/0008098 A1 Jan. 13, 2022

Related U.S. Application Data

(60) Division of application No. 15/894,294, filed on Feb. 12, 2018, now Pat. No. 11,134,981, which is a
(Continued)

(51) Int. Cl.
*A61F 2/95* (2013.01)
*A61B 17/00* (2006.01)
(Continued)

(52) U.S. Cl.
CPC .... *A61B 17/3423* (2013.01); *A61B 17/00234* (2013.01); *A61B 17/12036* (2013.01);
(Continued)

(58) Field of Classification Search
CPC . A61F 2/95; A61F 2/011; A61B 17/26; A61B 17/34; A61B 17/50; A61B 17/221;
(Continued)

(56) References Cited

U.S. PATENT DOCUMENTS

| 6,071,263 A | 6/2000 | Kirkman |
| 6,156,055 A | 12/2000 | Ravenscroft |

(Continued)

FOREIGN PATENT DOCUMENTS

| CA | 2366716 A1 | 9/2000 |
| CN | 104254287 A | 12/2014 |

(Continued)

OTHER PUBLICATIONS

"U.S. Appl. No. 14/498,493, Final Office Action mailed Jan. 14, 2016", 17 pgs.
(Continued)

*Primary Examiner* — Vi X Nguyen
(74) *Attorney, Agent, or Firm* — Schwegman Lundberg & Woessner, P.A.

(57) ABSTRACT

A device for providing access to a nodule, lesion, or pathological area in a lung or other body organ or lumen. The device includes a sheath portion having a proximal end and a distal end and a plurality of stabilization wires. The sheath portion includes a primary lumen that extends from the proximal end to the distal end and a plurality of secondary lumens that extend from the proximal end to the distal end. The stabilization wires are configured to be slidably received within the secondary lumens. The length of the stabilization wires is greater than the length of the secondary lumens.

10 Claims, 19 Drawing Sheets

Related U.S. Application Data continuation-in-part of application No. 14/498,493, filed on Sep. 26, 2014, now Pat. No. 10,258,376, which is a continuation of application No. PCT/US2013/031077, filed on Mar. 13, 2013.

(60) Provisional application No. 61/617,572, filed on Mar. 29, 2012.

(51) Int. Cl.

| | | |
|---|---|---|
| A61B 17/12 | (2006.01) | |
| A61B 17/34 | (2006.01) | |
| A61B 17/50 | (2006.01) | |
| A61M 25/00 | (2006.01) | |
| A61M 25/06 | (2006.01) | |
| A61B 17/22 | (2006.01) | |
| A61F 2/01 | (2006.01) | |
| A61M 25/04 | (2006.01) | |

(52) U.S. Cl.
CPC .. *A61B 17/12104* (2013.01); *A61B 17/12172* (2013.01); *A61B 17/50* (2013.01); *A61M 25/0082* (2013.01); *A61M 25/0662* (2013.01); *A61B 2017/00809* (2013.01); *A61B 2017/12054* (2013.01); *A61B 17/12177* (2013.01); *A61B 2017/22035* (2013.01); *A61F 2/011* (2020.05); *A61M 2025/0036* (2013.01); *A61M 2025/004* (2013.01); *A61M 2025/0096* (2013.01); *A61M 25/04* (2013.01)

(58) Field of Classification Search
CPC ........ A61B 17/32056; A61M 25/0082; A61M 25/0662; A61M 25/04
See application file for complete search history.

(56) References Cited

U.S. PATENT DOCUMENTS

| | | | |
|---|---|---|---|
| 6,293,951 | B1 | 9/2001 | Alferness et al. |
| 6,592,594 | B2 | 7/2003 | Rimbaugh et al. |
| 6,722,360 | B2 | 4/2004 | Doshi |
| 6,929,637 | B2 | 8/2005 | Gonzalez et al. |
| 7,533,671 | B2 | 5/2009 | Gonzalez et al. |
| 7,691,151 | B2 | 4/2010 | Kutsko et al. |
| 7,875,048 | B2 | 1/2011 | Dillard et al. |
| 7,993,362 | B2 * | 8/2011 | Lowe .................. A61F 2/0105 606/200 |
| 8,043,301 | B2 | 10/2011 | Adams et al. |
| 8,136,230 | B2 | 3/2012 | Adams et al. |
| 10,258,376 | B2 | 4/2019 | Dillard et al. |
| 11,134,981 | B2 | 10/2021 | Finger et al. |
| 2003/0154988 | A1 | 8/2003 | Devore et al. |
| 2003/0181922 | A1 | 9/2003 | Alferness |
| 2003/0181945 | A1 | 9/2003 | Opolski et al. |
| 2003/0195385 | A1 | 10/2003 | Devore |
| 2003/0212412 | A1 | 11/2003 | Dillard et al. |
| 2006/0184193 | A1 | 8/2006 | Lowe et al. |
| 2006/0206138 | A1 | 9/2006 | Eidenschink |
| 2006/0212042 | A1 | 9/2006 | Lamport et al. |
| 2008/0033451 | A1 | 2/2008 | Rieber et al. |
| 2009/0182370 | A1 | 7/2009 | Volobuyev et al. |
| 2010/0228281 | A1 | 9/2010 | Gilson et al. |
| 2010/0324588 | A1 * | 12/2010 | Miles .............. A61B 17/12122 606/198 |
| 2015/0080903 | A1 | 3/2015 | Dillard et al. |
| 2018/0161142 | A1 | 6/2018 | Finger et al. |

FOREIGN PATENT DOCUMENTS

| | | |
|---|---|---|
| CN | 104254287 B | 2/2017 |
| DE | 112013001718 T5 | 12/2014 |
| JP | H09327463 A | 12/1997 |
| JP | 2002538928 A | 11/2002 |
| JP | 2008113795 A | 5/2008 |
| JP | 2008529722 A | 8/2008 |
| JP | 2008229354 A | 10/2008 |
| JP | 2015514470 A | 5/2015 |
| JP | 2016179183 A | 10/2016 |
| JP | 6177307 B2 | 7/2017 |
| JP | 6181235 B2 | 7/2017 |
| WO | WO-2006028266 A1 | 3/2006 |
| WO | WO-2007079415 A2 | 7/2007 |
| WO | WO-2011043900 A1 | 4/2011 |
| WO | WO-2013148220 A1 | 10/2013 |

OTHER PUBLICATIONS

"U.S. Appl. No. 14/498,493, Final Office Action mailed Aug. 8, 2018", 13 pgs.
"U.S. Appl. No. 14/498,493, Final Office Action mailed Sep. 8, 2017", 18 pgs.
"U.S. Appl. No. 14/498,493, Non Final Office Action mailed Jan. 25, 2018", 17 pgs.
"U.S. Appl. No. 14/498,493, Non Final Office Action mailed Apr. 15, 2015", 8 pgs.
"U.S. Appl. No. 14/498,493, Non Final Office Action mailed Dec. 22, 2016", 20 pgs.
"U.S. Appl. No. 14/498,493, Notice of Allowance mailed Oct. 25, 2018", 8 pgs.
"U.S. Appl. No. 14/498,493, Response filed Apr. 4, 2016 to Final Office Action mailed Jan. 14, 2016", 8 pgs.
"U.S. Appl. No. 14/498,493, Response filed Apr. 19, 2018 to Non Final Office Action mailed Jan. 25, 2018", 9 pgs.
"U.S. Appl. No. 14/498,493, Response filed May 23, 2017 to Non Final Office Action mailed Dec. 22, 2016", 9 pgs.
"U.S. Appl. No. 14/498,493, Response filed Oct. 4, 2018 to Final Office Action mailed Aug. 8, 2018", 7 pgs.
"U.S. Appl. No. 14/498,493, Response filed Oct. 14, 2015 to Non Final Office Action mailed Apr. 15, 2015", 9 pgs.
"U.S. Appl. No. 14/498,493, Response filed Dec. 12, 2017 to Final Office Action mailed Sep. 8, 2017", 9 pgs.
"U.S. Appl. No. 15/894,294, Non Final Office Action mailed Jan. 25, 2021", 11 pgs.
"U.S. Appl. No. 15/894,294, Notice of Allowance mailed Jun. 9, 2021", 8 pgs.
"U.S. Appl. No. 15/894,294, Response filed Apr. 23, 2021 to Non Final Office Action mailed Jan. 25, 2021", 12 pgs.
"U.S. Appl. No. 15/894,294, Response filed Jul. 15, 2020 to Restriction Requirement mailed Dec. 19, 2019", 6 pgs.
"U.S. Appl. No. 15/894,294, Restriction Requirement mailed Dec. 19, 2019", 6 pgs.
"Chinese Application Serial No. 201380020525.5, Office Action mailed Jan. 29, 2016", w/ English translation, 27 pgs.
"International Application Serial No. PCT/US2013/031077, International Preliminary Report on Patentability mailed Oct. 9, 2014", 9 pgs.
"International Application Serial No. PCT/US2013/031077, International Search Report mailed May 31, 2013", 2 pgs.
"International Application Serial No. PCT/US2013/031077, Written Opinion mailed May 31, 2013", 7 pgs.
"Japanese Application Serial No. 2015-503283, Notice of Reasons for Refusal mailed Oct. 25, 2016", w/ English Translation, 10 pgs.
"Japanese Application Serial No. 2015-503283, Notice of Reasons for Refusal mailed Nov. 24, 2015", w/ English Translation, 12 pgs.
"Japanese Application Serial No. 2015-503283, Response filed Jan. 10, 2017 to Notice of Reasons for Refusal mailed Oct. 25, 2016", w/ English Translation, 5 pgs.
"Japanese Application Serial No. 2015-503283, Response filed May 12, 2016 to Notice of Reasons for Refusal mailed Nov. 24, 2015", w/ English Translation, 15 pgs.
"Japanese Application Serial No. 2016-096338, Notice of Reasons for Refusal mailed Nov. 22, 2016", w/ English Translation, 4 pgs.
"Japanese Application Serial No. 2016-096338, Response filed Feb. 14, 2017 to Notice of Reasons for Refusal mailed Nov. 22, 2016", w/ English Translation, 10 pgs.

(56) References Cited

OTHER PUBLICATIONS

"United Kingdom Application Serial No. 1415955.2, Examination Report under section 18(3) mailed May 15, 2015", 4 pgs.
"United Kingdom Application Serial No. 1415955.2, Examination Report under section 18(3) mailed Sep. 21, 2015", 59 pgs.
"United Kingdom Application Serial No. 1415955.2, Examination Report under section 18(3) mailed Nov. 6, 2014", 1 pg.
"United Kingdom Application Serial No. 1415955.2, Response filed Mar. 4, 2015 to Examination Report under section 18(3) mailed Nov. 6, 2014", 18 pgs.
"United Kingdom Application Serial No. 1415955.2, Response filed Sep. 3, 2015 to Examination Report under section 18(3) mailed May 15, 2015", 9 pgs.
U.S. Appl. No. 14/498,493 U.S. Pat. No. 10,258,376, filed Sep. 26, 2014, Medical Devices and Systems for Manipulating Foreign Bodies and Methods of Using the Same.
U.S. Appl. No. 15/894,294 U.S. Pat. No. 11,134,981, filed Feb. 12, 2018, Pulmonary Nodule Access Devices and Methods of Using the Same.

\* cited by examiner

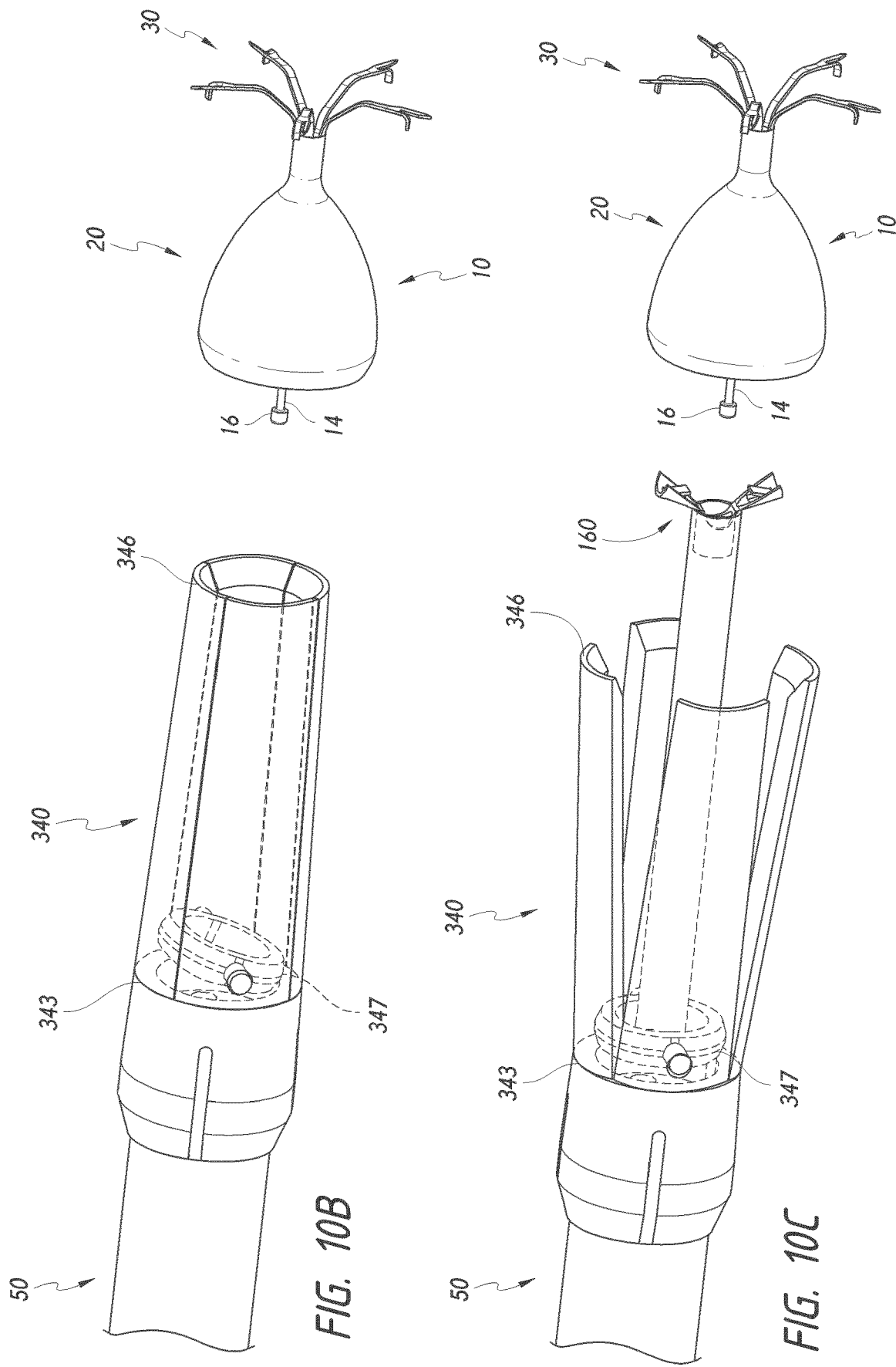

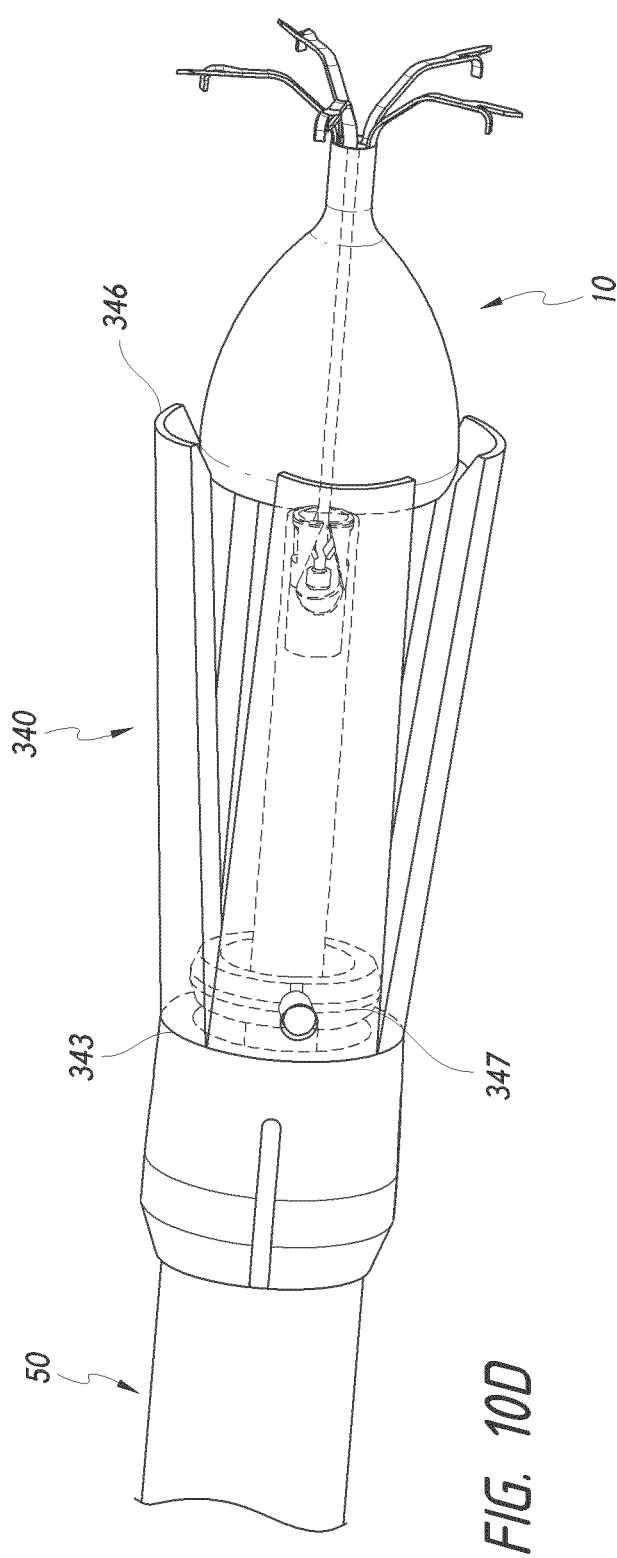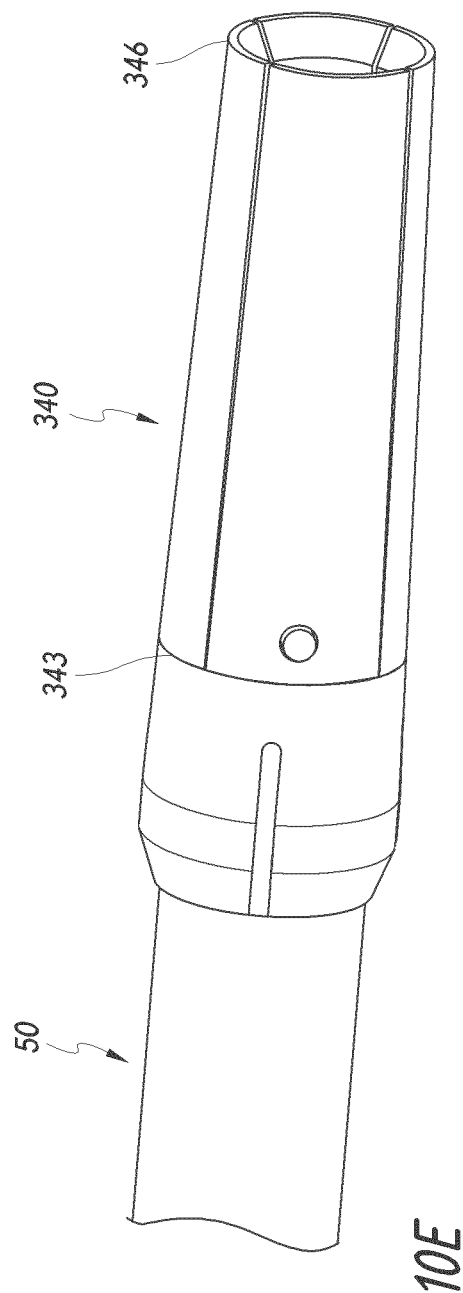

PULMONARY NODULE ACCESS DEVICES AND METHODS OF USING THE SAME

RELATED APPLICATION

This application is a Divisional of U.S. application Ser. No. 15/894,294 filed Feb. 12, 2018, which is a Continuation-in-Part of U.S. application Ser. No. 14/498,493 filed Sep. 26, 2014, and which is now U.S. Pat. No. 10,258,376, issued Apr. 16, 2019, which is a Continuation of International Application PCT/US2013/031077 filed Mar. 13, 2013, which claims priority to U.S. Provisional Application Ser. No. 61/617,572 filed Mar. 29, 2012.

BACKGROUND

Treatment or investigation of nodules, lesions, or pathological areas in the lung often requires repeated access to the same region of the lung. In some cases, test to determine whether the nodule is benign or malignant can take days or weeks and can require multiple biopsy samples from the same nodule. Treatment of malignant nodules can require further repeated access to treat the nodule. In cases where a nodule is located in the peripheral regions of the lung, navigation and access can be challenging because the small diameters of the airways in the peripheral regions of the lung do not admit to visual navigation. There is therefore a need for a device and method to safely, quickly, and consistently access the site of a nodule on a repeatable basis.

SUMMARY

In some embodiments, a device for providing access to a nodule, lesion, or pathological area in a lung or other body organ or lumen. The device includes a sheath portion having a proximal end and a distal end and a plurality of stabilization wires. The sheath portion includes a primary lumen that extends from the proximal end to the distal end and a plurality of secondary lumens that extend from the proximal end to the distal end. The stabilization wires are configured to be slidably received within the secondary lumens. The length of the stabilization wires is greater than the length of the secondary lumens.

In one aspect of the invention, the primary lumen includes a first interior dimension, the at least one of the secondary lumen includes a second interior dimension. The first interior dimension is larger than the second interior dimension.

In another aspect of the invention, the primary and secondary lumens include central longitudinal axes. The central longitudinal axes of the second lumens are located further from a center axis of the sheath portion than the central longitudinal axis of the primary lumen.

In still another aspect of the invention, the device further includes a stabilization wire control device that allows a user to control deployment of the one or more of the stabilization wires at the distal end of the sheath portion. The stabilization wire control device includes a handle portion configured to flexibly attach to proximal ends of the stabilization wires. The handle portion allows independent deployment of two or more of the stabilization wires.

In yet another aspect of the invention, at least one of the stabilization wires is keyed within a respective one of the second lumens.

In still yet another aspect of the invention, the stabilization wires deflect away from a center axis of the sheath portion. One or more of the stabilization wires includes a shape memory material.

Further features, advantages, and areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 10B is a view of the tool of FIG. 10A attached to the distal end of an endoscope;

FIG. 10C is a view of the tool of FIG. 10A in an expanded configuration;

FIG. 10D is a view of the tool of FIG. 10A partially-engaged with a medical device;

FIG. 10E is a view of the tool of FIG. 10A having a medical device loaded therein;

DETAILED DESCRIPTION

Devices and methods for repositioning within, and/or removing medical devices from, a patient now will be described with reference to the accompanying figures of one or more embodiments. The terminology used in the description presented herein is not intended to be interpreted in any limited or restrictive manner. Rather, the terminology is simply being utilized in conjunction with a detailed description of the embodiments of the devices and methods. For example, although reference is made to the removal and/or repositioning of medical valves within the body, this disclosure is not necessarily limited to medical valves. For instance, embodiments of the present disclosure may be used to remove and/or reposition implantable medical devices or medical devices accessed via or useable within, passages, vessels, cavities, lumens or the like (e.g., stents, plugs, ports, etc.). Furthermore, embodiments may comprise several novel features, no single one of which is solely responsible for its desirable attributes or is believed to be essential to practicing the methods and devices described herein. Although some embodiments described herein refer to removing and/or repositioning a medical device deployed in an airway, this disclosure is not so limited. For example, disclosed devices and methods can be used to remove medical devices from other vessels, passages, cavities and lumens in humans and animals. Additionally, in some embodiments, the removal and/or repositioning device can comprise a plurality of components that can be configured to connect to and/or disconnect from each other.

Additionally, throughout the specification, claims, and drawings, the term "proximal" means nearest the person or persons using the device, and "distal" means furthest from that person or those persons.

Figure 1:
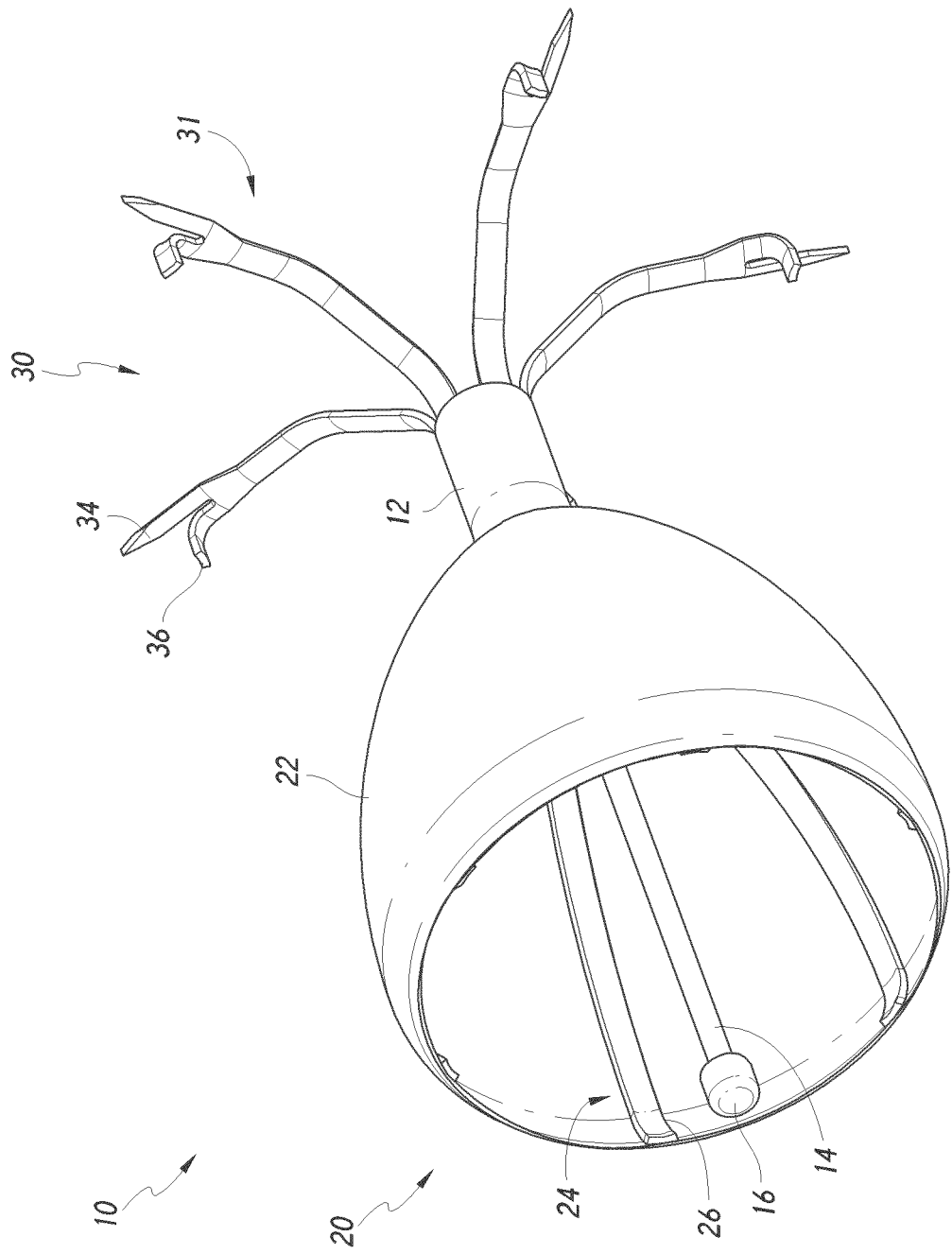
FIG. 1 is a perspective view of a medical valve.

FIG. 1 illustrates an embodiment of a removable medical device 10. In some embodiments, a removable medical device 10 can comprise a valve portion 20. In some embodiments, the valve portion 20 can connect to a hub 12. The valve portion 20 can have one or more struts 24 extending from the hub 12. In some embodiments, the valve portion 20 has a membrane portion 22. The membrane portion 22 can be configured to extend across the one or more struts 24. In some embodiments, the membrane portion 22 can extend across the outside (e.g., the side further from a central axis of the medical device 10) of the one or more struts 24. In some embodiments, the membrane portion 22 can extend across the inside of the one or more struts 24. In some embodiments, the ends of the struts 24 opposite the hub 12 can include turned portions 26. In some embodiments, the turned portions 26 are turned toward the central axis of the medical device 10. In some embodiments, the turned portions 26 are turned away from the central axis of the medical device 10.

In some embodiments, the removable medical device 10 can include a central rod 14. The rod 14 can be positioned along the central axis of the medical device 10. The rod 14 can be configured to attach to the hub 12. In some embodiments, the rod 14 extends in the same direction from the hub 12 as the valve portion 20. In some embodiments, the rod 14 extends in a direction from the hub 12 opposite the valve portion 20. In some embodiments, the rod 14 can have a cap 16 on the end of the rod 14 opposite the hub 12. In some embodiments, the rod 14 and/or cap 16 extend beyond the end of the valve portion 20 opposite the hub 12. In some embodiments, the cap 16 has a larger diameter or cross-section than the removal rod 14.

As illustrated in FIG. 1, the removable medical device 10 can have an anchor portion 30. The anchor portion 30 can attach to the hub 12. In some embodiments, the anchor portion 30 attaches to the portion of the hub 12 opposite the valve portion 20. In some embodiments, the anchor portion 30 is attached to the same portion of the hub as the valve portion 20. The anchor portion 30 can include one or more anchors 31. The one or more anchors 31 can attach to the hub 12. In some embodiments, the one or more anchors 31 attach to the portion of the hub 12 opposite the valve portion 20. In some embodiments, the anchors 31 attach to the same portion of the hub as the valve portion 20. In some embodiments, the anchors 31 include an anchor arm 32. In some embodiments, the anchors 31 include a piercing member 34 on the end of the anchors 31 opposite the hub 12. The piercing member 34 can be configured to penetrate the tissue of the walls in the region in which the medical device 10 is deployed. In some embodiments, the anchors 31 include a pad 36 adjacent the piercing member 24 on the end of the anchors 31 opposite the hub 12. In some embodiments, the pad 36 can limit the depth to which the piercing members 34 can penetrate tissue.

In some embodiments, the valve portion 20 can be configured to transition between a compressed configuration and an expanded configuration. For example, the struts 24 can be configured to compress inwardly toward the rod 14 upon the application of a compressing force on the struts 24 and/or membrane portion 22. In some embodiments, the struts 24 are biased to the expanded configuration. In some embodiments, the struts 24 are shape-set to the expanded configuration. In some embodiments, the struts 24 can be constructed of Nitinol or some other suitable material.

In some embodiments, the anchoring portion 30 can be configured to transition between a compressed configuration and an expanded configuration. For example, the anchors 31 can be configured to bend inwardly and away from the hub 12 upon application of a compressing force on the anchors 31. In some embodiments, the anchors 31 are biased to the expanded configuration. In some embodiments, the anchors 31 are shape-set to the expanded configuration. In some embodiments, the anchors 31 can be constructed of Nitinol or some other suitable material.

Figure 2A:
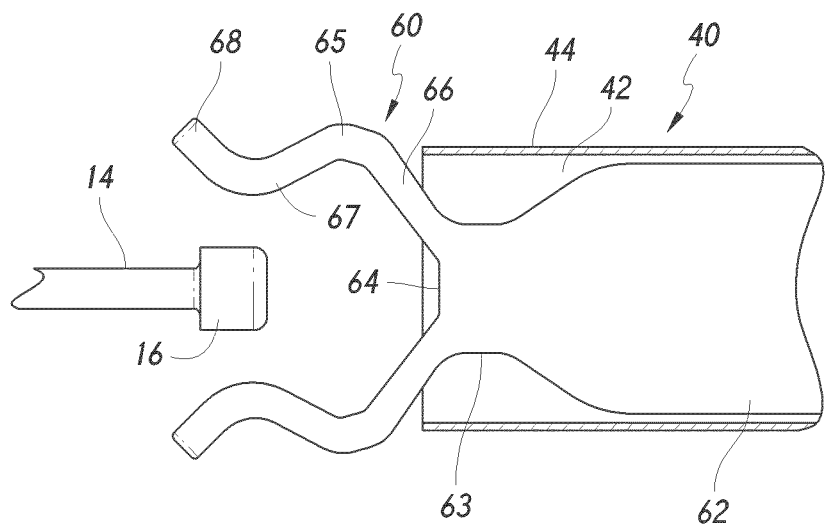
FIG. 2A is a view of a tool useful for repositioning or removing a medical device, which tool is shown in an opened configuration.
Figure 2B:
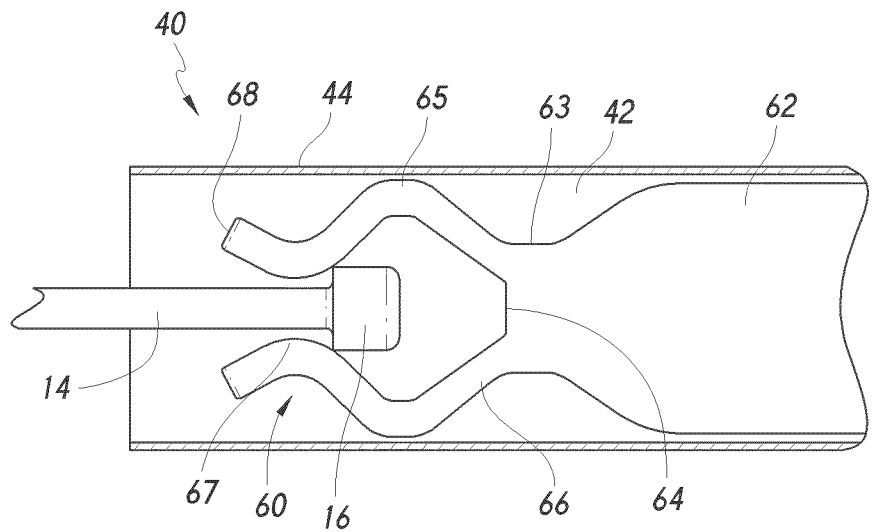
FIG. 2B is a view of the tool of FIG. 2A in a closed configuration.

FIGS. 2A and 2B illustrate an embodiment of an operative portion 60 of a tool that can be used for removing and/or repositioning a medical device 10. In some embodiments, the operative portion 60 can be configured to transition between an opened configuration (as illustrated in FIG. 2A)

and a closed configuration (as illustrated in FIG. 2B). In some embodiments, the removal device 60 can include a proximal portion 62. In some embodiments, the proximal portion 62 can be hollow. In some embodiments, at least a portion of the proximal portion 62 is solid. In some embodiments, the proximal portion 62 can be constructed of a rigid, semi-rigid, or flexible material. In some embodiments, the proximal portion 62 can be constructed of the same material as the remainder of the operative portion 60 of the tool for removing and/or repositioning a medical device 10. In some configurations, the proximal portion 62 and the operative portion 60 can be integrally formed or monolithic in configuration.

In some embodiments, the operative portion 60 can include one or more engagement members 66. In some embodiments, the one or more engagement members 66 are attached to the distal end of the proximal portion 62. The one or more engagement members 66 can be configured to be moveable toward one another. In some embodiments, movement of the one or more engagement members 66 toward one another can transition the operative portion 60 to the closed configuration. In some embodiments, movement of the one or more engagement members 66 away from one another can transition the operative portion 60 to the opened configuration. In some embodiments, the one or more engagement members 66 can be biased to the opened configuration. In some embodiments, the operative portion 60 can include one or more indentations 63. In some embodiments, the indentations 63 can reduce the force required to transition the one or more engagement members 66 between the opened configuration and the closed configuration.

The one or more engagement members 66 can include an expanded portion 65 connected to the distal end of the proximal portion 62. In some embodiments, the expanded portion 65 extends outwardly from the proximal portion 62 with respect to a central axis of the operative portion 60 when the operative portion 60 is in the closed configuration. In some embodiments, the expanded portion 65 extends outwardly with respect to the central axis of the operative portion 60 from a connection point between the engagement members 66 and the proximal portion 62 when the operative portion 60 is in the opened or closed configuration. In some embodiments, the connection between the engagement members 66 and the proximal portion 62 defines a proximal backstop 64 (e.g., when the proximal portion 62 comprises a solid part). In some embodiments, the engagement members 66 have a grasping portion 67. In some embodiments, the grasping portion 67 can be attached to the distal end of the expanded portion 65. In some embodiments, the grasping portion 67 can extended inwardly with respect to the central axis of the operative portion 60 from the expanded portion 65.

In some embodiments, the operative portion 60 includes distal tips 68 on the ends of the engagement members 66. In some embodiments, the distal tips 68 of the engagement members can be connected to the distal ends of the grasping portions 67. In some embodiments, the distal tips 68 extend outwardly from the grasping portions 67 with respect to the central radius of the operative portion 60. In some embodiments, the distal tips 68 define atraumatic structures such that any body structure can be somewhat protected during contact between the distal tips 68 and the body structure. The distal tips 68 and/or other portions of the engagement members 66 can be configured to widen the body structure (e.g., a body lumen such as an airway) within which the engagement members 66 are transitioned to the opened configuration. For example, the engagement members 66 (or some portion thereof) can widen the body lumen in which a device 10 is implanted. In some embodiments, widening of the body lumen in which a device 10 is implanted can help to disengage the device 10 (or some portion thereof) from the walls of the body lumen (e.g., help to disengage the device 10 from surrounding hyperplastic portions of the body lumen).

Figure 2C:
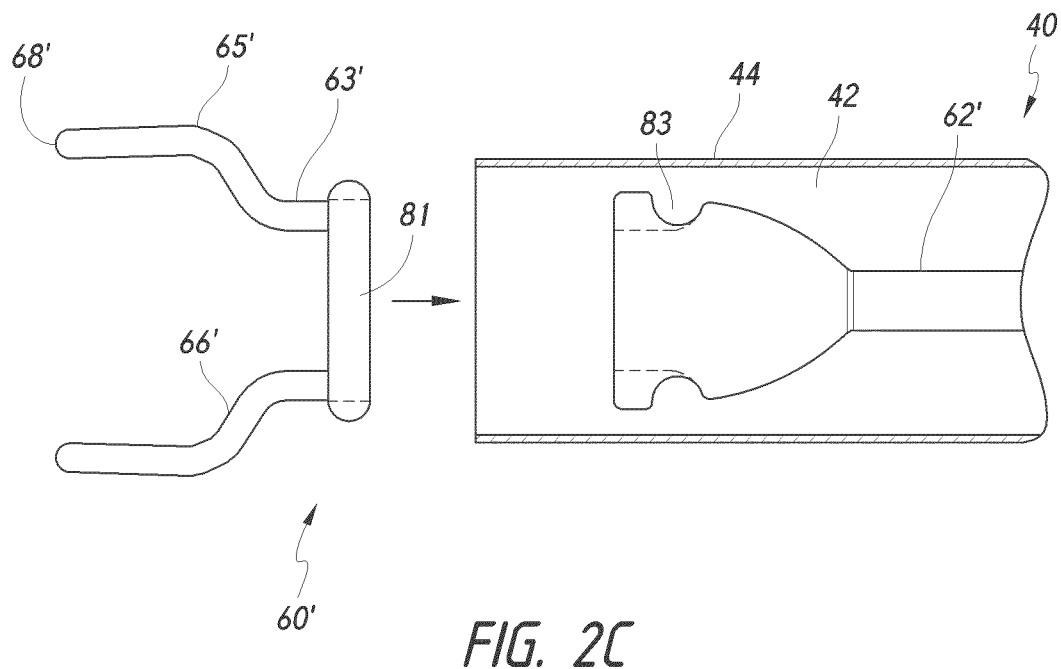
FIG. 2C is a view of another tool with a removable portion in the detached and opened configuration.
Figure 2D:
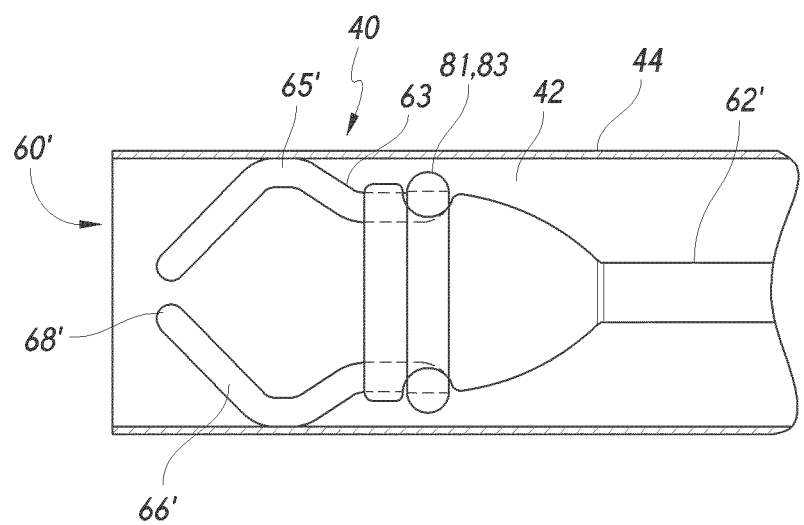
FIG. 2D is a view of the tool of FIG. 2C in the attached and closed configuration.

FIGS. 2C and 2D illustrate an embodiment of an operative portion 60' of a tool that can be used for removing and/or repositioning a foreign body (e.g. a medical device). Some numerical references to components in FIGS. 2C and 2D are the same or similar to those previously described for the operative portion 60 described above except that prime (') has been added. It is to be understood that the components can be the same in function or are similar in function to previously-described components. The operative portion 60' of FIGS. 2C and 2D shows certain variations to the operative portion 60 of FIGS. 2A and 2B.

In some embodiments, the engagement portions 66' are removable from the proximal portion 62'. In some embodiments, the proximal portion 62' includes a groove 83. The proximal ends of the engagement portions 66' can be configured to connect with a band 81. The band 81 can be constructed of nitinol or any other suitable material. In some embodiments, the band 81 can be configured to removably engage with the groove 83. In some embodiments, the engagement members 66' can be constructed of nitinol or any other suitable material. In some embodiments, the engagement member 66' and the band 81 form a unitary part. In some embodiments, the engagement members 66' can be biased in the opened configuration.

Figure 3A:
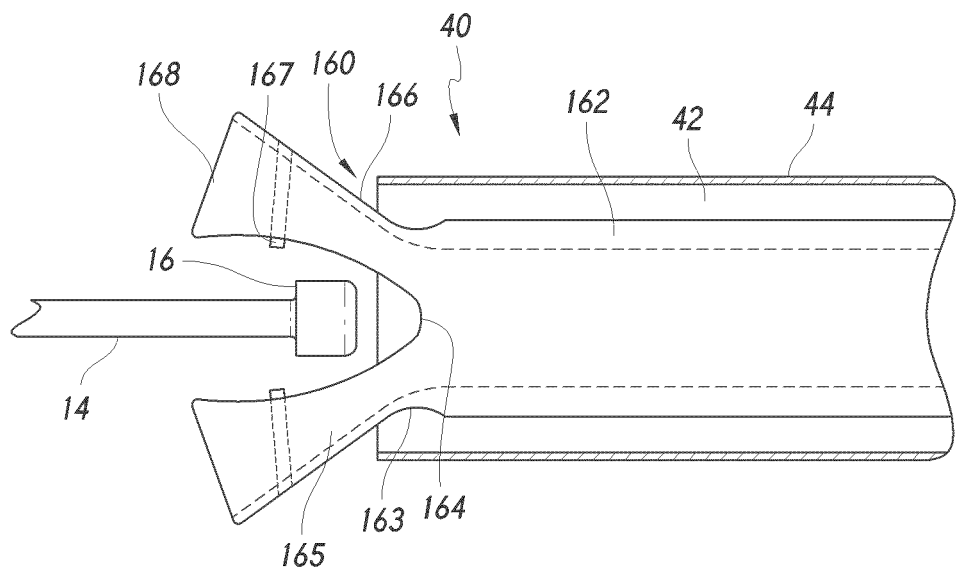
FIG. 3A is a view of another tool in an opened configuration.

FIGS. 3A-4B illustrate an embodiment of an operative portion 160 of a tool that can be used for removing and/or repositioning a medical device 10. In some embodiments, the operative portion 160 can be configured to transition between an opened configuration (as illustrated in FIG. 3A) and a closed configuration (as illustrated in FIG. 3B). In some embodiments, the operative portion 160 can include a proximal portion 162. In some embodiments, the proximal portion 162 is hollow. In some embodiments, at least a portion of the proximal portion 162 is solid. In some embodiments, the proximal portion 162 can be constructed of a rigid, semi-rigid, or flexible material. In some embodiments, the proximal portion 162 can be constructed of the same material as the remainder of the operative portion 160 of the tool for removing and/or repositioning a medical device 10. In some embodiments, the operative portion 160 is formed from a tubular piece of material (e.g. Nitinol or some other suitable material). In some configurations, the proximal portion 162 and the operative portion 160 can be monolithic in configuration or integrally formed.

In some embodiments, the operative portion 160 includes one or more engagement members 166. The engagement members 166 can extend distally from the proximal portion 162. In some embodiments, the engagement members 166 include expanded portions 165. The expanded portions 165 can extend outwardly away from a central axis of the operative portion 160 when the operative portion 160 is in the opened or closed configuration. In some embodiments, the expanded portion 165 can extend in the distal direction substantially parallel to the walls of the proximal portion 162 when the operative portion 160 is in the closed configuration. In some embodiments, the expanded portion 165 can extend inwardly toward the central axis of the operative portion 160 when the operative portion 160 is in the closed configuration.

In some embodiments, the engagement members 166 can include one or more grasping portions 167. In some embodiments, the grasping portions 167 extend inwardly from the engagement members 166 toward the central axis of the operative portion 160. In some embodiments, the grasping portions 167 extend inwardly as well as in the proximal direction. In some embodiments, the grasping portions 167 extend inwardly as well as in the distal direction. In some embodiments, the grasping portions 167 are formed by making two or more cuts in the engagement members 166 and bending the cut portion of the engagement members 166 inwardly toward the central axis of the operative portion 160. In some embodiments, the grasping portions 167 are formed by making at least two substantially parallel cuts in the engagement members 166 and flexing the cut portion inwardly toward the central axis of the operative portion 160. In some embodiments, the grasping portions 167 are formed by making at least two cuts in the engagement members 166, each cut extending to a distal end 168 of the engagement members 166 such that the cut portion can be folded down toward the central axis of the operative portion 160 to form the grasping portions 167. In some embodiments, the radial length of each of the grasping portions 167 is less than half the length of the inner diameter of the engagement members 166. In some embodiments, the radial length (e.g., the length substantially perpendicular to the central axis of the operative portion 160) of each of the grasping portions 167 is less than half the distance between the inner walls of the engagement members 166. In some embodiments, the total radial length of the one or more grasping portions 167 is less than the distance between the inner walls of the engagement members 166.

Figure 3B:
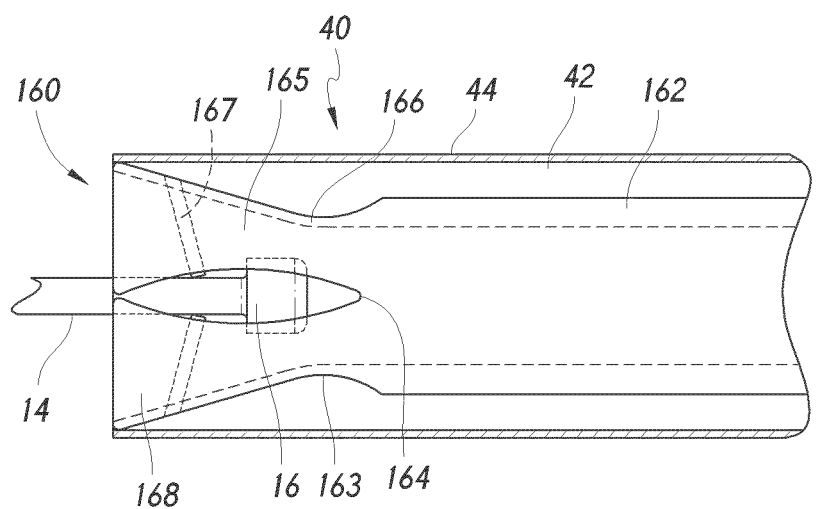
FIG. 3B is a view of the tool of FIG. 3A in a closed configuration.

In some embodiments, the connection between the engagement members 166 and the proximal portion 162 can form a back portion 164. In some embodiments, the distal ends 168 of the engagement members 166 can come into contact with each other when the operative portion 160 is in a closed configuration. In some embodiments, the distal ends 168 of the engagement members 166 can have a semicircular or curved shape (e.g. when viewed along the central axis of the operative portion 160). In some embodiments, the distal ends 168 of the engagement members 166 can be flat (e.g. when viewed along the central axis of the operative portion 160). In some embodiments, the space formed between the back portion 164 and engagement members 166 can form substantially "tear drop" shaped space when the operative portion 160 is in a closed configuration, as illustrated in FIG. 3B.

In some embodiments, the operative portion 160 can include one or more indentations 163. In some embodiments, the indentations 163 can be located near the proximal ends of the engagement members 166. In some embodiments, a thickness of the indentations 163 in a direction substantially perpendicular to the central axis of the operative portion 160 can be less than a thickness of the operative portion 160 distal and/or proximal of the indentations 163 in the direction substantially perpendicular to the central axis of the operative portion 160. The indentations 163 can decrease the force required to transition the operative portion 160 between the opened configuration and the closed configuration.

In some configurations, a method of removing and/or repositioning a medical device 10 from an airway or other body lumen can include the step of grasping the medical device 10 using the operative portion 160 of a tool for removing and/or repositioning a medical device 10. For example, with reference to FIGS. 3A-4B, the operative portion 160 of the tool for removing and/or repositioning a medical device 10 can be include a sleeve 40. In some embodiments, the sleeve 40 can be a catheter, the working channel of an endoscope, or any other suitable lumen, conduit, or tube. In some embodiments, the sleeve 40 includes a sleeve lumen 42. In some embodiments, the sleeve 40 includes sleeve walls 44. In some embodiments, the total radial length of the one or more grasping portion 167, the diameter of the rod 14 of the medical device 10, and the wall thicknesses at the distal end of the two or more engagement member 166 can be less the inner diameter of the sleeve 40.

In some embodiments, the sleeve 40 can be moved in the distal and/or proximal directions with respect to the operative portion 160. As described above, the engagement members 166 of the operative portion 160 can be biased to the opened configuration. In some configurations, the engagement members 166 can be configured to transition to the closed configuration when the sleeve 40 moves over the distal ends 168 of the engagement members 166, as illustrated, for example, in FIGS. 3B and 4B. In some embodiments, the engagement members 166 can be configured to transition to the opened configuration when the distal end of the sleeve 40 is moved from beyond the distal ends 168 of the engagement members 166 to proximal of the engagement members 166. As explained above with reference to FIGS. 2A-2B, the engagement member 166 can be configured to expand the body lumen in which the engagement members 166 are transitioned to the opened configuration. In some embodiments, expansion of the body lumen by the engagement members 166 (or some portion thereof) can help to disengage a target device 10 (e.g., a device to be removed) from adjacent portions of the body lumen (e.g., hyperplastic portions of the body lumen).

In some embodiments, the tool for removing and/or repositioning medical devices can include a stabilizing portion proximal of the proximal portion 162 of the operative portion 160. The stabilizing portion can allow the operative portion 160 to be held in place within the body of the patient while the sleeve 40 is moved in the proximal and/or distal directions with respect to the operative portion 160. In some embodiments, the stabilizing portion can be a wire extending in the proximal direction from the proximal end of the proximal portion 162. In some embodiments, the stabilizing portion can be a tube extending in the proximal direction from the proximal end of the proximal portion 162. In some embodiments, the proximal portion 162 can be a unitary part with the stabilizing portion. In some embodiments, the stabilizing portion can allow the user of the operative portion 160 to move the operative portion 160 in the distal and/or proximal directions with respect to the sleeve 40.

Figure 4A:
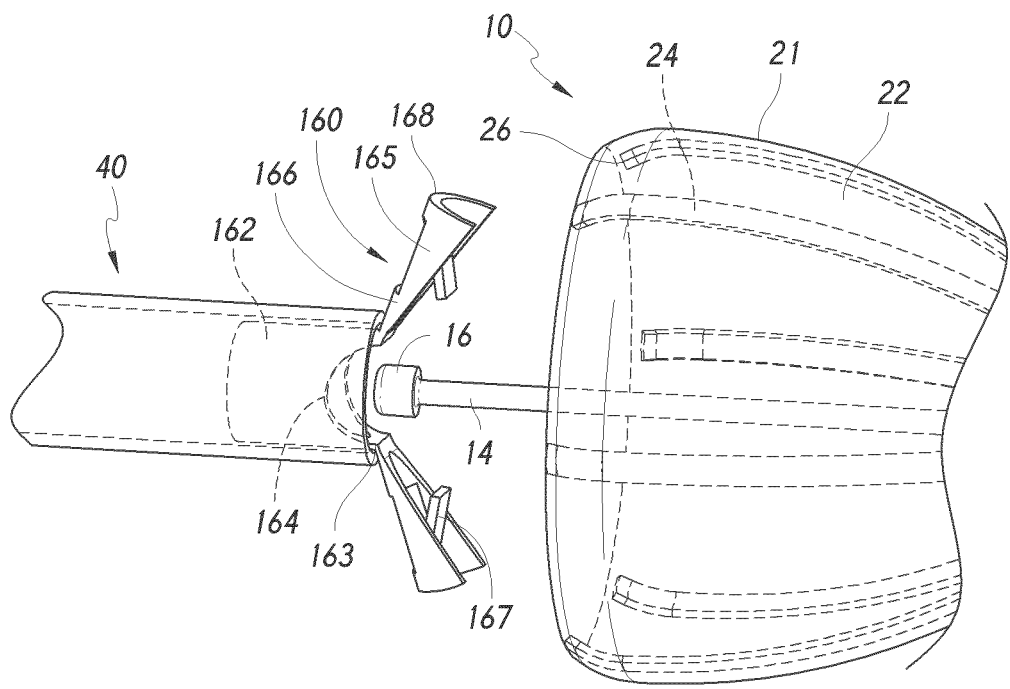
FIG. 4A is a perspective view of the tool of FIG. 3A in an opened configuration.
Figure 4B:
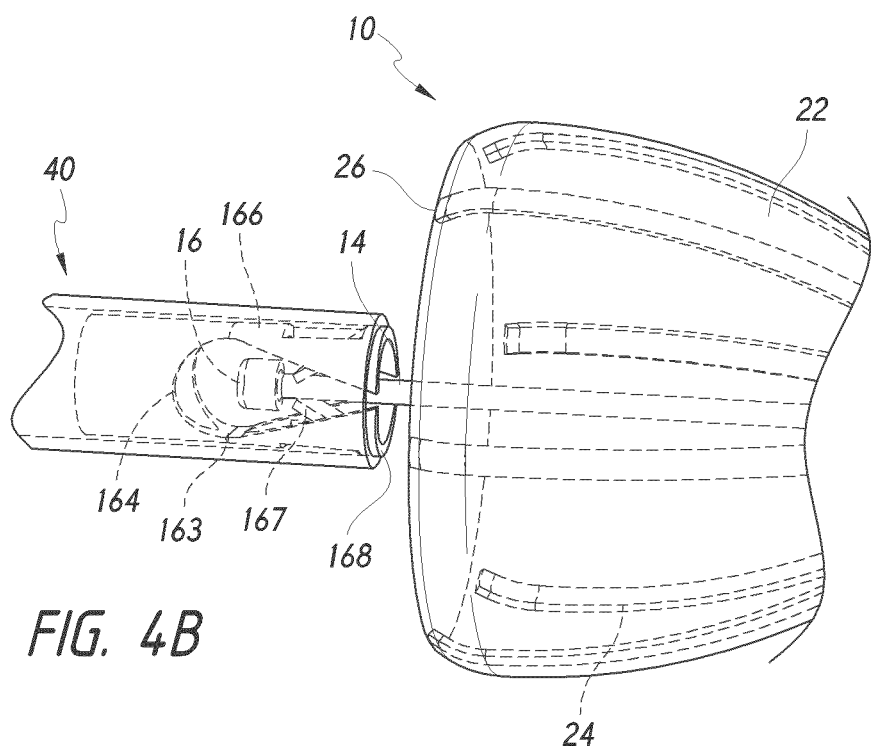
FIG. 4B is a perspective view of the tool of FIG. 3A in a closed configuration.

With reference to FIGS. 3A and 4A, the operative portion 160 can be positioned near the cap 16 on the end of the central rod 14 of a medical device 10. In some embodiments, the sleeve 40 can be withdrawn from the operative portion 160 in the proximal direction. The engagement members 166 then can transition to the opened configuration. The operative portion 160 then can be moved toward the central rod 14 of the medical device 10 until the central rod 14 and/or cap 16 are positioned within the engagement members 166 such that the cap 16 is located proximal to the grasping portions 167, as illustrated, for example, in FIGS. 3A and 4A. The sleeve 40 then can be moved distally with respect to the operative portion 160 so that the engagement members 166 transition toward the closed configuration, as illustrated, for example, in FIGS. 3B and 4B.

In some embodiments, the grasping portions 167 can secure the cap 16 within the operative portion 160 when the engagement members 166 are transitioned to the closed configuration while the cap 16 is located proximal to the grasping portions 167. The operative portion 160 then can be used to pull the medical device 10 in the proximal direction. In some embodiments, the operative portion 160 can be configured to push the medical device 10 in the distal direction when the cap 16 is secured within the operative portion 160.

Figure 3C:
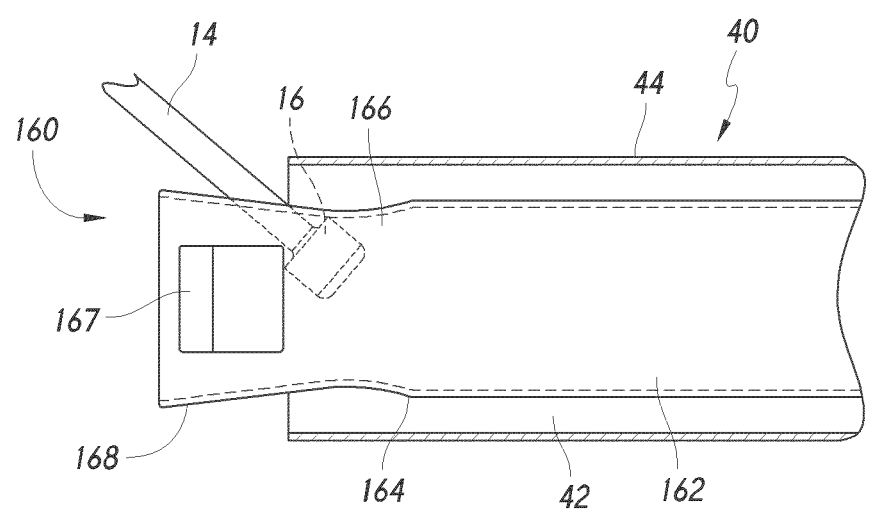
FIG. 3C is a view of the tool of FIG. 3A in a closed configuration grabbing an off-axis device.

In some embodiments, the "tear drop" shaped space formed by the back portion 164 and engagement members 166 can make it easier for the user of the operative portion 160 to grasp a cap 16 on the end of a central rod 14 in situations where the central axes of the medical device 10 and operative portion 160 are not aligned with one another, as illustrated in FIG. 3C. In such a situation, the operative portion 160 can, in some embodiments, be used to pull the medical device 10 in the proximal direction and/or push the medical device 10 in the distal direction.

Although a method of grasping a medical device 10 has been described in the context of the embodiment of the operative portion 160 illustrated in FIGS. 3A-4B, the same general method can be performed using the embodiment of the operative portion 60 found in FIGS. 2A and 2B.

Figure 5:
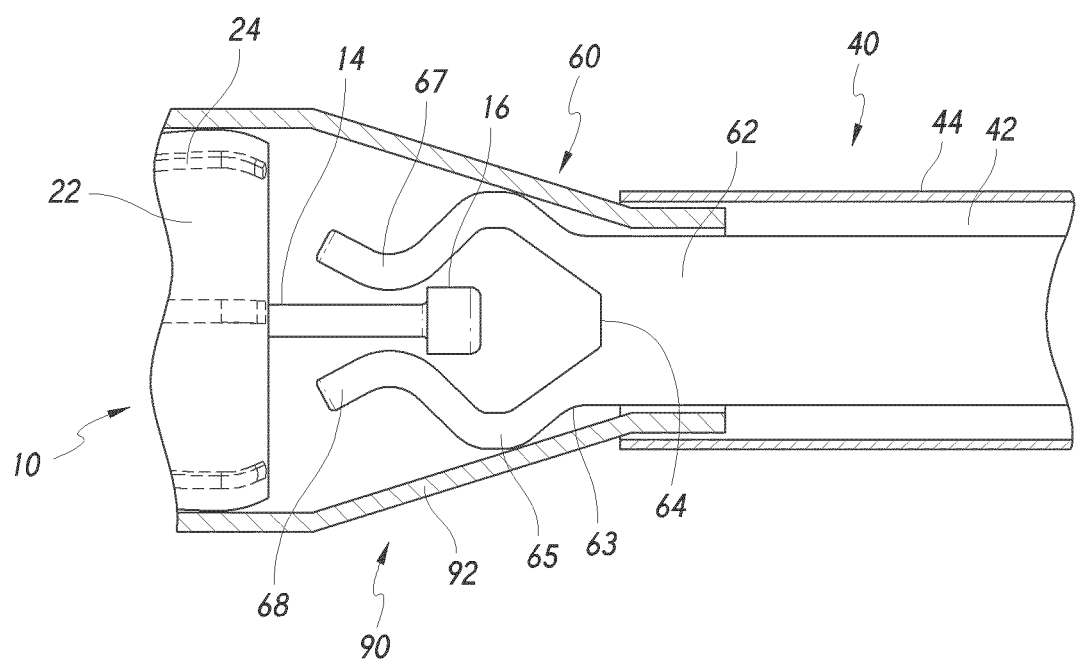
FIG. 5 is a view of a tool engaged with a valve loading tool.

FIG. 5 illustrates a method of using the operative portion 60 of a tool for removing and/or repositioning medical devices 10 to pull a medical device 10 through the interior of a compressing device 90 into the interior of the sleeve 40. In some embodiments, the compressing device 90 can include a tapered portion 92. The tapered portion 92 can be constructed from a flexible or semi-flexible material configured to stretch and/or bend when in contact with the medical device 10 and/or with the walls of the body lumen in which the medical device 10 is implanted. In some embodiments, the tapered portion 92 is constructed from a rigid or semi-rigid material. The operative portion 60 can be used to grasp the cap 16 on the end of the central rod 14 and pull the device 10 toward the sleeve 40. In some embodiments, the tapered portion 92 can help transition the struts 24 and/or anchors 31 of the device 10 from the expanded configuration to the compressed configuration as the device 10 is pulled toward the sleeve 40. Examples of tapering devices can be found in U.S. Pat. Nos. 8,043,301 and 8,136,230, which are hereby incorporated by reference herein in their entireties.

Figure 6:
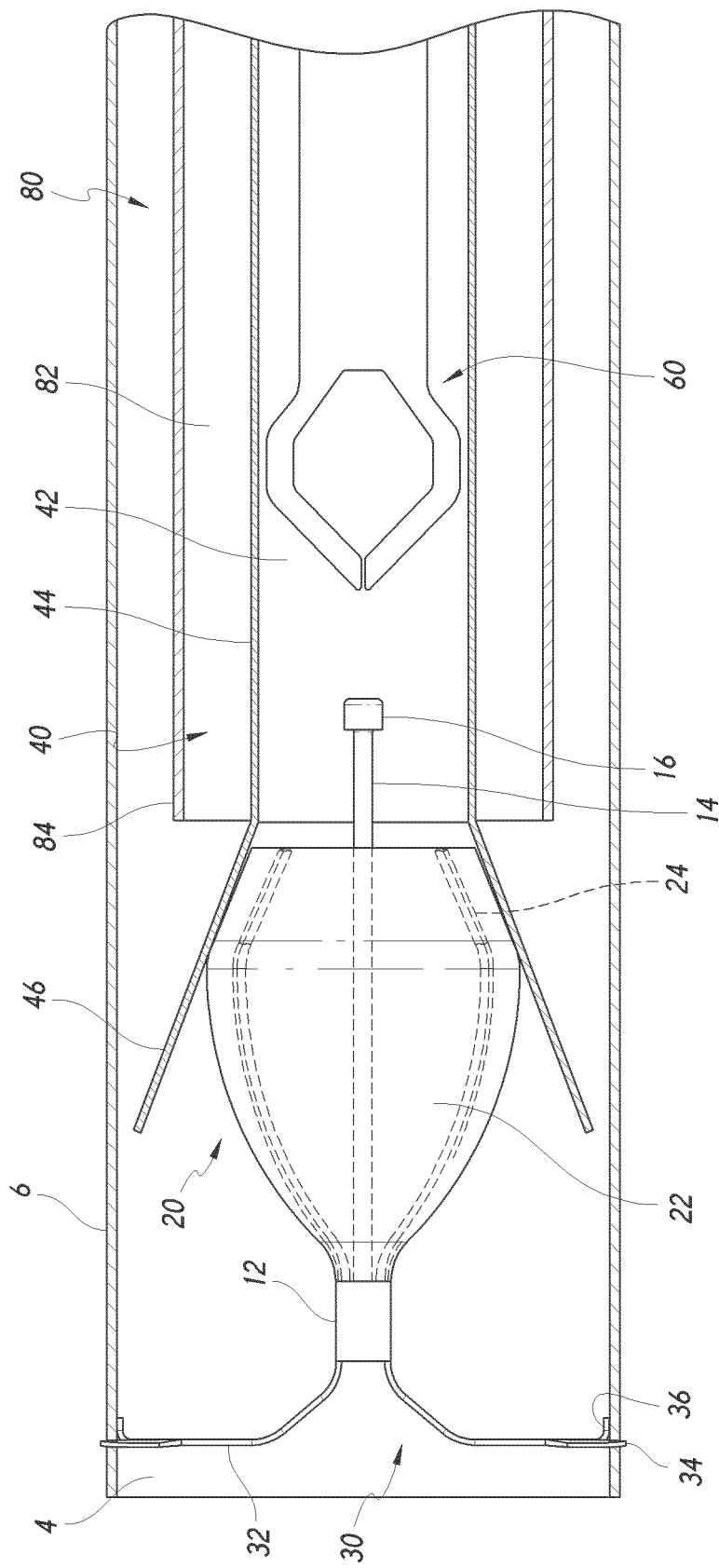
FIG. 6 is a view of a tool having a flared distal end.
Figure 7:
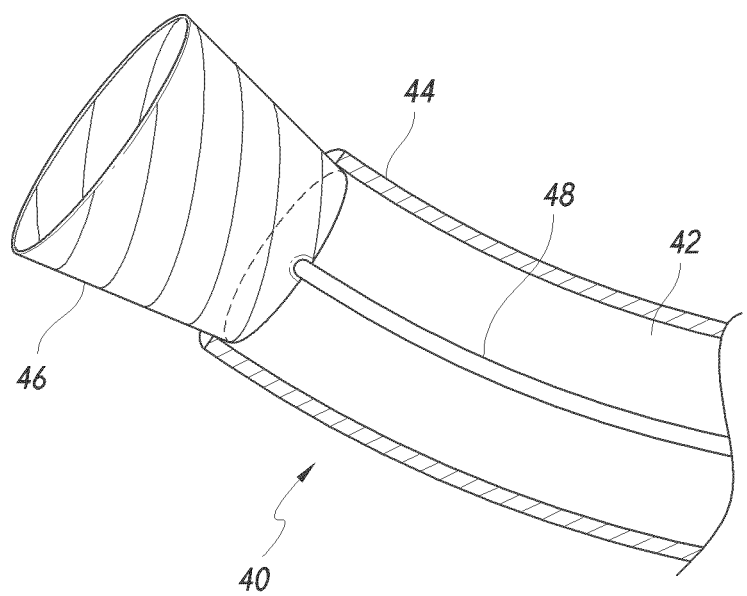
FIG. 7 is a view of a tool having a spiral flared distal end.

In some embodiments, a tool for removing and/or repositioning medical devices 10 can include a compressing portion 46. In some embodiments, the compressing portion 46 is conical or frustoconical in shape, as illustrated in FIGS. 6 and 7. In some embodiments, the compressing portion 46 is fluted (e.g., the radius of the compressing portion 46 increases at a decreasing rate toward the distal end of the compressing portion 46) or trumpeted (e.g., the radius of the compressing portion 46 increases at an increasing rate toward the distal end of the compressing portion 46) in shape. In some embodiments, the compressing portion 46 can have fluted portions, trumpeted portions, conical portions, frustoconical portions, or any combination thereof. In some embodiments, the compressing portion 46 is attached to the distal end of the sleeve 40. The sleeve 40 can be delivered to site of the medical device 10 via a working channel 82 of a deliver device 80 (e.g., a working channel of a catheter, bronchoscope, endoscope, or other delivery device). In some embodiments, the compressing portion 46 is attached to a rod or wire 48. In some embodiments, the compressing portion 46 is attached to the wire 48 via welding, adhesives, soldering, magnets, or some other suitable method of affixing the wire 48 to the compressing portion 46. In some embodiments, the compressing portion 46 can be moved in the distal and/or proximal direction with respect to the sleeve 40. In some embodiments, the compressing portion 46 can be moved in the distal and/or proximal direction with respect to the operative portion 60. In some embodiments, the compressing portion 46 is fixed to the sleeve 40. In some embodiments, the compressing portion 46 is a unitary part with the sleeve 40.

The compressing portion 46 can be constructed of a rigid, semi-rigid, or flexible material. In some embodiments, the compressing portion 46 is constructed of the same material as the sleeve 40 and/or the operative portion 60. In some embodiments, the compressing portion 46 is constructed of Nitinol or some other shape memory material. The compressing portion 46 can be constructed of a series of overlapping spiraled panels, as illustrated in FIG. 7. In some embodiments, the compressing portion 46 can be constructed of a single piece of material. In some embodiments, the compressing portion 46 can have a window cut into to allow for visualization through the compressing portion 46.

In some embodiments, the compressing portion 46 can be configured to transition between a compressed configuration and an expanded configuration. In some embodiments, the compressing portion 46 is configured to transition from the compressed configuration to the expanded configuration (e.g., as illustrated in FIG. 6) upon withdrawal of the delivery device 80 from the compressing portion 46. In some embodiments, the compressing portion 46 can be biased to the expanded configuration, as illustrated in FIGS. 6 and 7. For example, the compressing portion 46 can be biased to the expanded configuration such that, as the distal end 84 of the delivery device 80 is withdrawn from the compressing portion 46, the compressing portion 46 expands within the airway 4 or other body lumen. In some embodiments, compressing portion 46 can be configured to transition to the compressed configuration when the compressing portion 46 is positioned within the sleeve 40 or some other lumen or conduit (e.g. the working channel of an endoscope). In some configurations, the compressing portion 46 can be configured to at least partially retract into the sleeve 40. In some embodiments, the compressing portion 46 can be configured to apply expansive force upon and expand the tissue 6 of an airway 4 or other body lumen when the compressing portion 46 is in the expanded configuration.

Figure 8A:
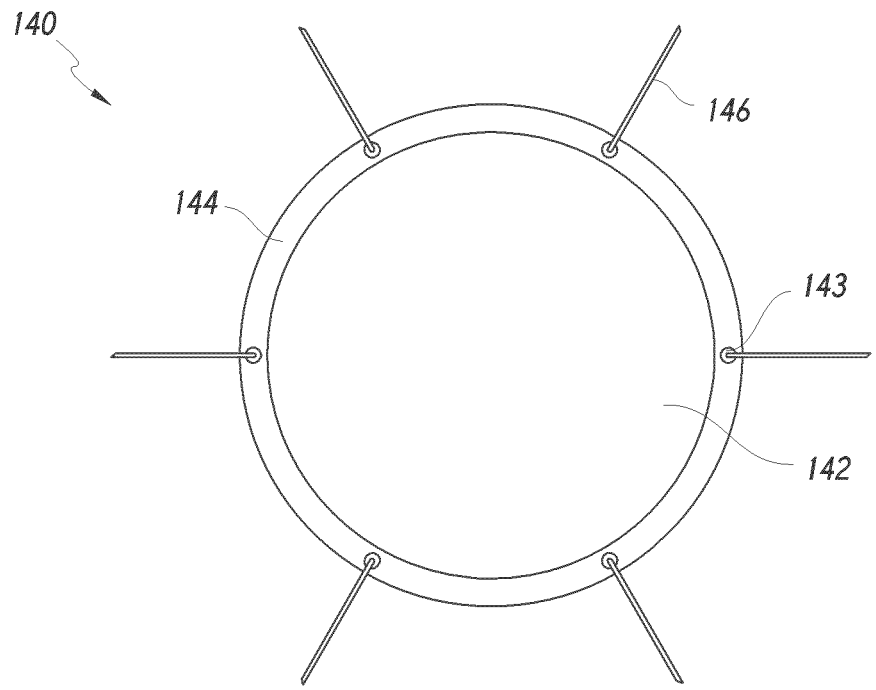
FIG. 8A is a distal end view of a multi-lumen tool having a plurality of guide-wires.
Figure 8B:
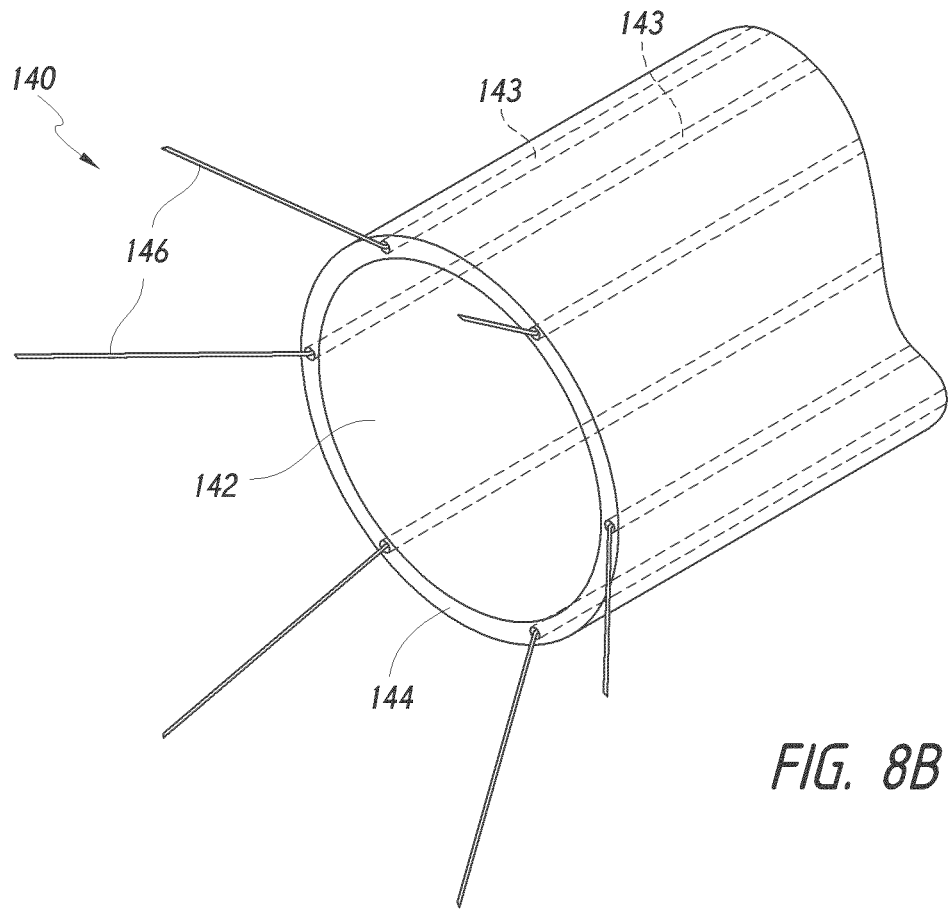
FIG. 8B is a perspective view of the multi-lumen tool of FIG. 8A.
Figure 8C:
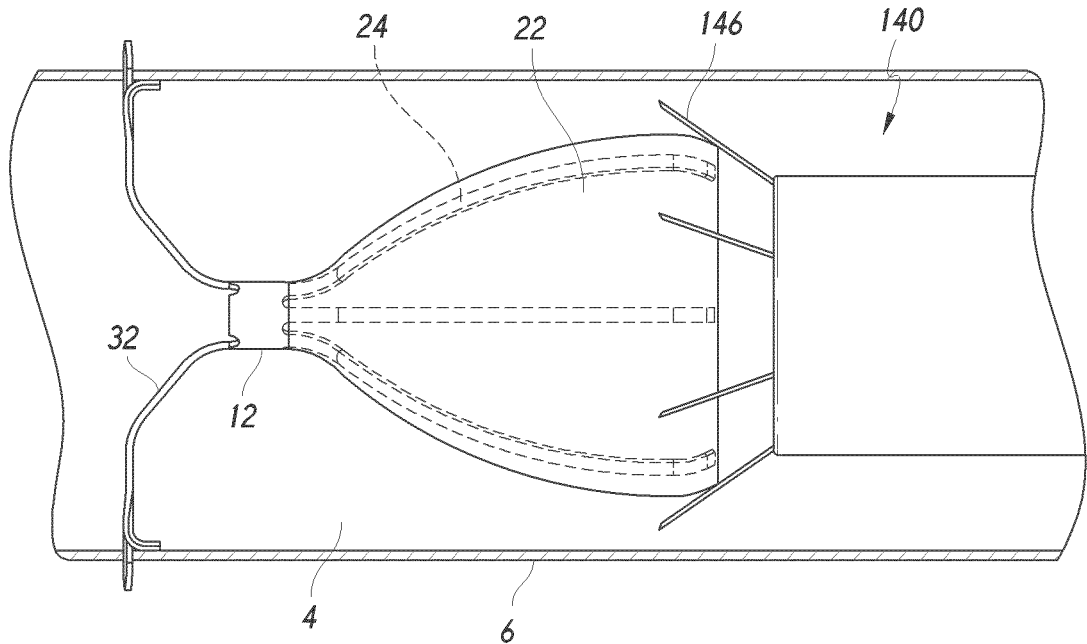
FIG. 8C is a view of the multi-lumen tool of FIG. 8A within an airway or other body lumen.

In some embodiments, the tool for removing and/or repositioning medical devices can include a plurality of compression wires 146, as illustrated in FIGS. 8A and 8B. The compression wires 146 can be housed in one or more secondary conduits 143 within a sleeve 140. In some embodiments, the number of compression wires 146 and/or corresponding secondary conduits 143 used can match the number of struts 24 on the medical device 10 to be removed/repositioned. In some embodiments, the number of wires 146 and/or corresponding secondary conduits 143 used can be fewer than the number of struts 24. In some embodiments, the number of wires 146 and/or corresponding secondary conduits 143 can be more than the number of struts 24. In some embodiments, the compression wires 146 can be configured to transition from a compressed configuration to an expanded configuration upon extension of the wires 146 from the secondary conduits 143. In some embodiments, the compression wires 146 can be configured to transition from the expanded configuration to the closed configuration upon the return of the wires 146 into the secondary conduits 143. In some embodiments, the compression wires 146 can be constructed of Nitinol or some other suitable material. In some embodiments, the compression wires 146 can include a stabilizing member. In some embodiments, the stabilizing member can have a circular or semi-circular shape and can extend between each of the individual compression wires 146 (e.g. on or more rings of material which connect one or more of the individual compression wires 146 to each other). In some embodiments, the stabilizing member can limit movement of the compression wires 146 in the tangential direction (e.g., tangential with respect to the central axis of the sleeve 140) toward or away from each other. In some configurations, the stabilizing member can form a loop that somewhat controls a diameter to which the wires can expand.

Figure 8D:
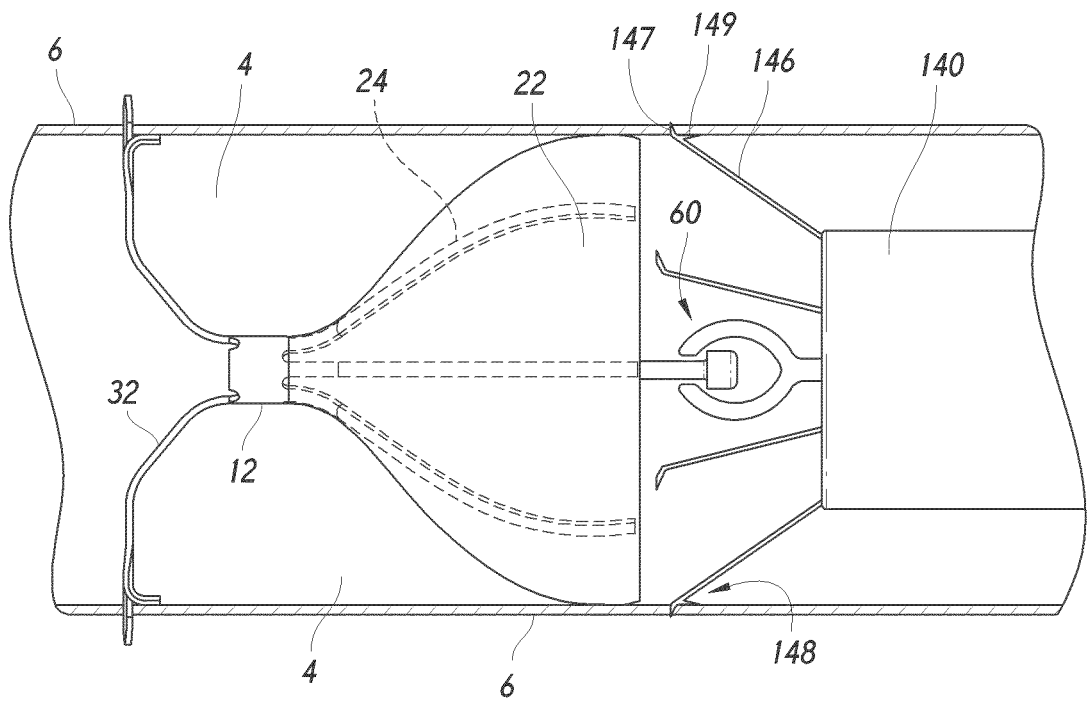
FIG. 8D is a view of an embodiment of the tool of FIG. 8A having distal anchors on the guide-wires.

In some embodiments, the wires 146 can include anchoring portions. In some configurations, the anchoring portions can be formed on the distal ends of the wires 146, as illustrated in FIG. 8D. In some embodiments, the anchoring portions of the wires 146 can include a piercing member 147. In some embodiments, the piercing members 147 can be configured to penetrate the tissue 6 of an airway 4 or other body lumen when the wires 146 are in the expanded configuration. In some embodiments, the anchoring points of the wires 146 can include pads 149. The pads 149 can be configured to limit the depth to which the piercing members 147 can penetrate the tissue 6.

The wires can have any desired cross-section. The cross-section can be substantially uniform along the length of the wire or the cross-section can vary. In some embodiments, a tool for removing and/or repositioning a medical device 10 can include a plurality of flat compression wires 246. The flat wires 246 can be housed within a plurality of secondary conduits 243 within a sleeve 240. The flat wires 246 can be configured to transition from a compressed configuration to an expanded configuration upon extension of the flat wires 246 from the secondary conduits 243. In some embodiments, the flat wires 246 can be configured to transition from the expanded configuration to the compressed configuration upon the return of the flat wires 246 into the secondary conduits 243.

A method of compressing a medical device 10 into a device to remove and/or reposition a medical device 10 can include the step of grasping the cap 16 on the end of a rod 14 of the medical device 10, as described above. In some embodiments, the method can include transitioning the compressing portion 46 to the expanded configuration, as illustrated in FIG. 6. The operative portion 60 then can be used to pull the medical device 10 toward the compressing portion 46 or to hold the medical device 10 stable while the compressing portion 46 is advanced toward the medical device 10. In some embodiments, the operative portion 60 can be used to hold the medical device 10 in place as the compressing portion 46 is moved toward the medical device. As the medical device 10 is received into the compressing portion 46, the flared shape of the compressing portion 46 can cause the medical device 10 to transition to a compressed configuration. For example, the struts 24 of the medical device 10 can come into contact with the compressing portion 46 and can be urged toward the central rod 14 of the medical device 10. Compression of the struts 24 can cause the valve portion 20 of the medical device 10 transition to the compressed configuration. In some embodiments, the anchors 31 of the medical device 10 can be configured such that the piercing members 34 of the anchors 31 disengage from the tissue 6 as a result of the bending of the anchors 31 when the medical device 10 is pulled in the proximal direction.

In some embodiments, the operative portion 60 can continue to pull the medical device 10 toward the sleeve 40 such that the anchors 31 are brought into contact with the compressing portion 46. In some embodiments, the operative portion 60 can continue to hold the medical device 10 stable while the compressing portion 46 is advanced further toward the medical device 10. In some embodiments, the compressing portion 46 is configured to compress the anchors 31 to a compressed position as the anchors 31 travel through the compressing portion 46 toward the sleeve 40. In some embodiments, the entire medical device 10 can be transitioned into the sleeve 40 prior to the medical device 10 being removed and/or repositioned. In some embodiments, at least or only a portion of the medical device 10 can be transitioned into the sleeve 40. In some embodiments, the medical device 10 is not transitioned into the sleeve 40 as the medical device 10 is removed and/or repositioned. In some embodiments, the anchors 31 can be captured and/or covered by the tool such that, as the captured device 10 is moved within the body, the tool can reduce the likelihood that the anchors 31 or other portions of the medical device 10 could damage tissue within the body of the patient (e.g., the vocal chords, airways, trachea, or other body parts).

In some embodiments, the tool for repositioning and/or removing medical devices 10 can be moved within the body after the medical device 10 is removed from a first position. In some embodiments, the tool can be used to move the medical device 10 to a second location within the body. In such embodiments, the operative portion 60, compressing portion 46 and/or sleeve 40 can be moved to the second location in the body. In some embodiments, the sleeve 40 and/or the compressing portion 46 can include visual and/or radiopaque markings. The markings can be visualized using a camera within the delivery device, fluoroscopy, and/or any other visualization known by those skilled in the art. The markings can provide visual and/or fluoroscopic verification of the position of the tool and/or the position of the compressed medical device 10 within the tool. In some embodiments, a user of the tool can position the tool in the second location using the markings as a guide. The markings can include one or more colored bands, pigmented bands, metallic bands, translucent portions, and/or any other appropriate means or structure for allowing the user to visualize the location of the tool and/or the medical device 10. In some embodiments, the markings are located on the distal end of the sleeve 40 and/or the compressing portion 46. In some embodiments, the markings identify the location of a specific portion (e.g., the hub, proximal end of the struts, distal end of the anchors, etc.) of the medical device 10 within the sleeve 40.

Once positioned in the second location, the sleeve 40 and/or compressing portion 46 of the device can be withdrawn from (e.g. moved proximally with respect to) the operative portion 60. In some embodiments, as the sleeve 40 and/or compressing portions 46 are withdrawn from the operative portion 60 and/or medical device 10, the medical device 10 is configured to transition to an expanded configuration at the second location. In some embodiments, withdrawal of the sleeve 40 from the operative portion 60 can allow the engagement members 66 to transition to the opened configuration and can allow the grasping portions 67 to disengage from the medical device 10. In this manner, a medical device 10 can be deployed in a second location within the body.

Although the method of compressing and removing/repositioning a medical device 10 has been described with respect to the embodiment of the device illustrated in FIG.

Figure 8E:
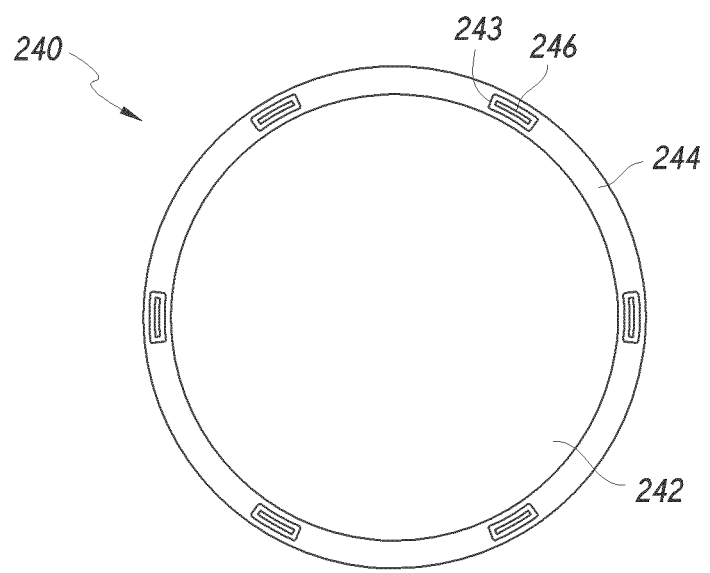
FIG. 8E is a distal end view of an embodiment of the tool of FIG. 8A having flat guide-wires.

6, the method can be similarly implemented using the embodiments of the device found in FIGS. 7-8E. For example, the compression wires 146 can be used to compress the valve portion 20 of the medical device 10 as the operative portion 60 pulls the medical device toward the sleeve 146. In some embodiments, the compression wires 146 can engage with the membrane portions 22 between the struts 24. In some embodiments, the compression wires 146 can penetrate built up tissue (e.g., hyperplasia) surrounding the valve portion 20 and can help remove the valve portion 20 of the medical device 10 from the walls of an airway 4 or other body lumen. In some embodiments, the anchor portions on the ends of the compression wires 146 can help hold the compression wires 146 in place as the valve portion 20 is compressed and can help reduce deflection of the compression wires 146 as the medical device 10 is pulled toward the sleeve 140. In some embodiments, the anchor portions on the ends of the compression wires 146 can be configured to release from the tissue 6 of the airway 4 when the compression wires 146 are pushed in the distal direction. In some embodiments, the anchor portions on the ends of the compression wires 146 can be configured to release from the tissue 6 of the airway 4 when the compression wires 146 are pulled in the proximal direction. In some embodiments, using flat compression wires 246 can help reduce the likelihood that the wires 246 will rotate with respect to the central axis of the operative portion 60, 160 and/or the central axes of the respective secondary conduits 243 as the medical device 10 is pulled toward the sleeve 240. In some embodiments, contact between the distal end of the sleeve 40, 140, 240 and the anchors 31 of the medical device 10 can cause the anchors 31 to transition to a compressed configuration.

Figure 9:
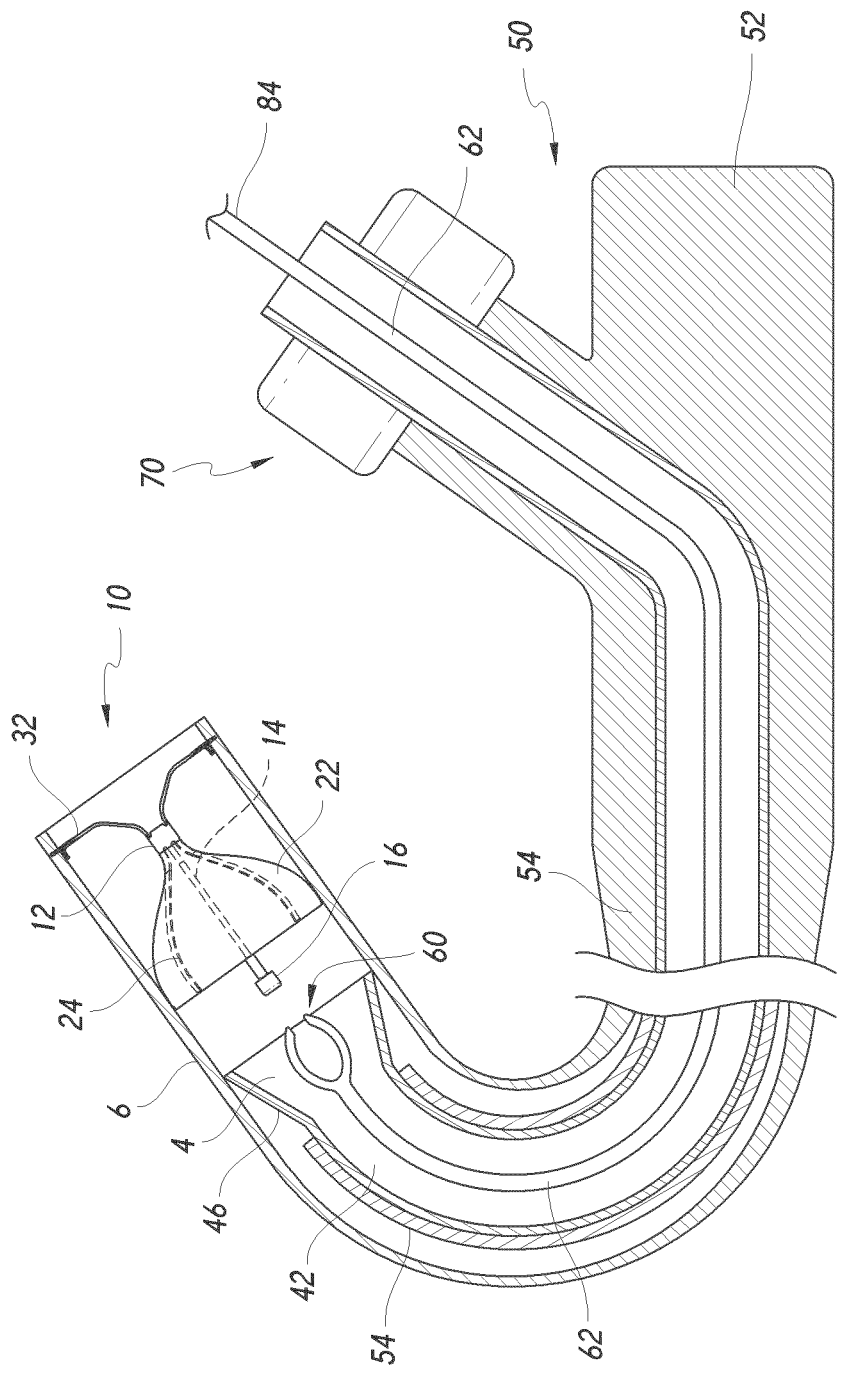
FIG. 9 is a view of a tool deployed within an airway or other body lumen via a working channel within an endoscope.

FIG. 9 illustrates an embodiment of the tool for removing and/or repositioning medical devices configured for use in an endoscope 50 or other delivery device. In some embodiments, the tool can be positioned within a working channel 54 of the endoscope 50. In some embodiments, the endoscope 50 or other delivery device can be used to navigate the tool through the patient's body to the site of a target medical device 10. The endoscope 50 can be guided from outside of the patient's body into an airway 4 of other body lumen. In some embodiments, a lock 70 can be used to hold portions (e.g., the operative portion 60, sleeve 40, and/or compressing portion 46) of the tool static with respect to the patient's body, the endoscope 50, and/or the other portions of the tool. In some embodiments, the lock 70 can be partially or completely released to allow for controlled movement of the portions of the tool with respect to one another (e.g., moving the sleeve in the distal and/or proximal direction with respect to the operative portion 60). The endoscope 50 can include a handle portion 52. In some embodiments, the handle portion 52 includes one or more controls or other user inputs (e.g., light controls, articulation controls, a vacuum control).

FIGS. 10A-10E illustrate an embodiment of a tool for repositioning and/or removing a medical device. The tool can include a capture portion 340. The capture portion 340 can include a body portion 342 with a proximal end 345. The proximal end 345 of the capture portion 340 can be configured to removably connect with the distal end of an endoscope 50 or other delivery device via the use of an adhesive, friction fitting, threading, magnets, or any other suitable method of adhering. The capture portion 340 can include one or more compression members 346. The compression members 346 can include hinge portions 343 where the compression members 346 connect to the body portion 342 of the capture portion 340. In some embodiments, capture portion 340 can include a single compression member 346. In some embodiments, the compression member 346 can have a conical shape, a fluted shape, a trumpeted shape, or any combination thereof. In some embodiments, the compression member 346 can be constructed of a single piece of material. In some embodiments, the compression member 346 can be constructed of overlapping panels of material. In some embodiments, the compression member 346 can be constructed of a plurality of wires. In some embodiments, the compression member 346 can be constructed of a plurality of woven wires.

In some embodiments, the compression members 346 can be configured to transition between an expanded configuration (as illustrated in FIGURE IOC) and a compressed configuration (as illustrated in FIGURE IOB) by moving about the hinge portions 343. In some embodiments, the one or more compression members 346 can be fixed in the expanded configuration. In some embodiments, the compression members 346 can be biased to the compressed configuration. In some embodiments, the compression members 346 can be biased to the expanded configuration. In some embodiments, the compression members 346 can be constructed of Nitinol or some other suitable material. In some embodiments, the compression members 346 can be transitioned to the expanded configuration by rotating a central ring 347 of the capture portion 240. The central ring 347 can be configured to rotate about an axis of rotation normal to or otherwise off axis from the central axis of the capture portion 340. In some embodiments, rotation of the central ring 347 can exert force on the interior of the compression members 346 such that the compression members transition to the expanded configuration. For example, the central ring 347 can be elliptical in shape such that a major diameter of the central ring 347 causes the ring 347 to come into contact with the compression members 346 when the central ring 347 is rotated toward coaxial (with respect to the central axis of the capture portion 340) alignment with the capture portion 340.

In some embodiments, each of the compression members 346 can include one or more internal lumens in communication with one or more internal lumens in the body portion 342. The one or more internal lumens can house a plurality of actuating wires. The actuating wires can have a bent shape such that, as the wires are extended from the body portion 342 into the lumens of the compression members 346, the wires can exert a radially-outward force on the compression members 346. In some embodiments, such a radially-outward force can cause the compression members 346 to transition from the compressed configuration to the expanded configuration. In some embodiments, the one or more internal lumens can house a plurality of actuating rods. In some embodiments, the actuating rods are straight. The actuating rods can be configured to extend and retract from the internal lumens of the body portion 342 into and out of the internal lumens of the compression members 346. In some embodiments, where the compression members 346 are biased to the expanded configuration, insertion of the actuating rods into the internal lumens of the compression members 346 can cause the compression members 346 to transition from the expanded configuration to the compressed configuration.

In some embodiments, the capture portion 340 can include an operative portion 160. In some embodiments, the operative portion 160 of the capture portion 340 is the same as or similar in both function and structure to the operative portion 160 described above. In some embodiments, the operative portion 160 of the capture portion 340 is the same as or similar in both function and structure to the operative portion 60 described above. In some embodiments, the operative portion 160 can be housed within a working channel of the endoscope 50. In some embodiments, the operative portion 160 can be housed within the capture portion 340.

Figure 10A:
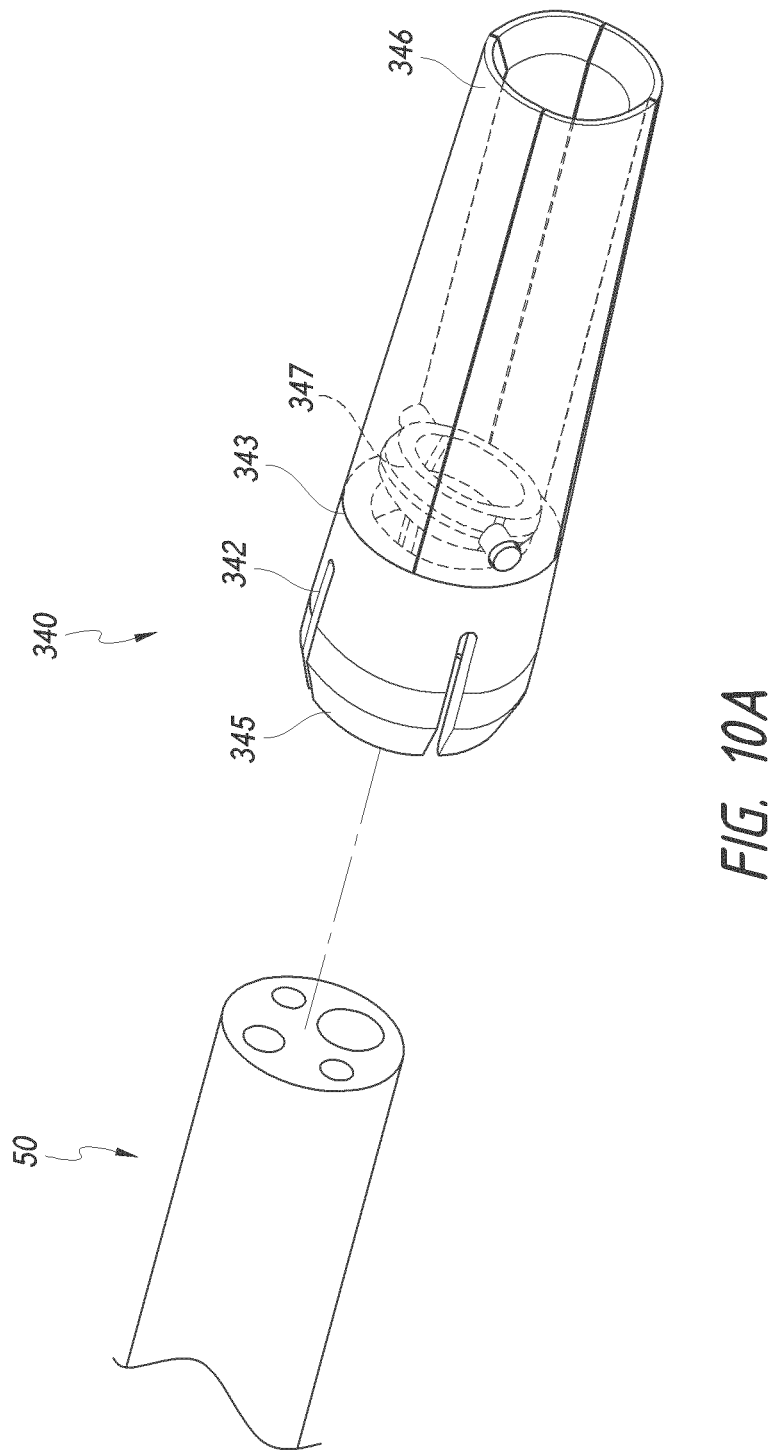
FIG. 10A is a view of a tool configured to be detachable from the distal end of an endoscope.

A method of using the tool illustrated in FIGS. 10A-10E to remove and/or reposition a foreign body (e.g., a medical device 10) can include attaching the proximal end 345 of the capture portion 340 to the distal end of the endoscope 50, as illustrated in FIG. 10A. In some embodiments, the method then can include guiding the capture portion 340 to the site of a medical valve 10, as illustrated in FIG. 10B. In some embodiments, the method can include expanding the compression members 346 to the expanded configuration via rotation of the central ring 347 or through application of other forces upon the compression members 346. In some embodiments, expansion of the compression members 346 can expand the tissue in the vicinity of the capture portion 340. Expansion of the tissue in the vicinity of the capture portion 340 can help to disengage the medical valve 10 from the surrounding tissue (e.g., disengage hyperplastic tissue from the medical valve 10). In some embodiments, the one or more compression members 346 can be fixed in the expanded configuration.

In some embodiments, the method can further include using the operative portion 160 of the capture portion 340 to grab the cap 16 of the medical device 10 in a manner similar to that described above. The operative portion 160 then can be used to pull the medical device 10 in the proximal direction toward the endoscope 50, as illustrated in FIG. 10D. In some embodiments, the operative portion 160 can be used to hold the medical device 10 stable as the capture portion 340 is transitioned toward the medical device 10. As the medical device 10 is approaches the endoscope 50, the struts 24 and/or membrane portion 22 of the medical device 10 can come into contact with the compression members 346. Such contact, as the medical device 10 is pulled toward the endoscope 50, can cause the valve portion 20 to transition to a compressed configuration. In some embodiments, the medical device 10 can be pulled in the proximal direction such that the anchors 31 come into contact with the compression members 346. Such contact can facilitate transition of the anchors 31 from the expanded configuration to the compressed configuration. In some embodiments, the entirety of the medical device 10 can be pulled into the capture portion 340. In some embodiments, the compression members 346 then can be transitioned to a compressed configuration, as illustrated in FIG. 10E. In some embodiments, the one or more compression members 346 can remain in the expanded configuration. In some embodiments, the endoscope 50 then can be used to remove the capture portion 340 and medical device 10 from the patient.

In some embodiments, the endoscope 50 can be used to navigate the capture portion 340 and medical device 10 to another location within the patient's body. In some embodiments, the compression members 346 then can be transitioned to the expanded configuration. The operative portion 160 then can be used to push the medical device 10 in the distal direction out from the capture portion 340. In some embodiments, the compression members 346 can be moved in the proximal direction with respect to the operative portion 160. The medical device 10 then can transition to an expanded configuration and can engage with the tissue surrounding the medical device 10. The operative portion 160 then can be transitioned to the opened configuration to release the medical device 10 from the tool for removing and/or repositioning medical devices. In some embodiments, the endoscope 50 then can be used to navigate the capture portion 340 out of the patient's body.

Although the tool for removing and/or repositioning medical devices has been disclosed in the context of certain embodiments and examples, those skilled in the art will understand that the present disclosure extends beyond the specifically disclosed embodiments to other alternative embodiments and/or uses of the tool and obvious modifications and equivalents thereof. In addition, while several variations of the tool have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of this disclosure. It should be understood that various features and aspects of the disclosed embodiments can be combined with, or substituted for, one another in order to form varying modes or embodiments of the tool. Thus, it is intended that the scope of the present disclosure should not be limited by the particular disclosed embodiments described above.

The device shown in FIGS. 8A-E can be modified to provide repeatable access to nodules, lesions, or pathological areas in the lung or other bodily organ. The terminology used in the description presented herein is not intended to be interpreted in any limited or restrictive manner. Rather, the terminology is simply being utilized in conjunction with a detailed description of embodiments of the devices and methods. For example, the term "nodule" can refer to lesions, tumors, or other pathologies within the body, independent of size and shape.

Some or all of the following embodiments herein disclosed can be utilized to provide repeatable access to a nodule or other site of interest for sampling, taking biopsies, or otherwise diagnosing the site of interest. Furthermore, some or all of the embodiments can be used to provide repeatable access to a site of interest for the purpose of providing treatment to the site of interest. For example, the embodiments herein may be utilized to provide repeatable access to the site(s) of interest for the purpose of administering medicants (e.g., chemotherapy) and/or administering energy and/or therapeutic seeds to the site of interest. Tools for draining infections (e.g., loculated infections) and/or bullae, providing antibiotics, and/or for introducing sealants to a site of interest can be used with some or all of the embodiments described herein.

Furthermore, embodiments may include several novel features, no single one of which is solely responsible for its desirable attributes or is believed to be essential to practicing the inventions herein described. Although some embodiments described herein refer to deploying an access device into an airway, this disclosure is not so limited, and deployment could be made, for example but without limitation, into other vessels, passages, and body cavities in humans and animals. Additionally, the embodiments described herein could be configured to be removable or permanent, depending on the purpose behind deploying the given embodiment in a given procedure. In some embodiments, the device can include a plurality of components which can be configured to connect to and/or disconnect from each other (e.g. proximal, central, and distal components). In such embodiments, the device can be configured to be completely (e.g. all components) removable and/or partially removable (e.g. some components). Some embodiments of the device can be completely permanent (e.g. all components permanently deployed) and/or partially permanent (e.g. some components removable). Some of the embodiments described herein can be used in conjunction with a number of treatment and/or diagnosis instruments (e.g. cytology brushes, RF probes, ultrasound probes, biopsy forceps, TBNA needles, etc.). Each of the embodiments described herein could include radiopaque markings or other visualization aids (e.g. markings compatible with x-ray, CT and/or bronchoscopic visualization) to assist a care provider in navigating, deploying, and/or locating the device. Some of the embodiments described herein can include laser cut patterns, side passageways, or other features detectable by an ultrasound probe or other visualization device.

Figure 11:
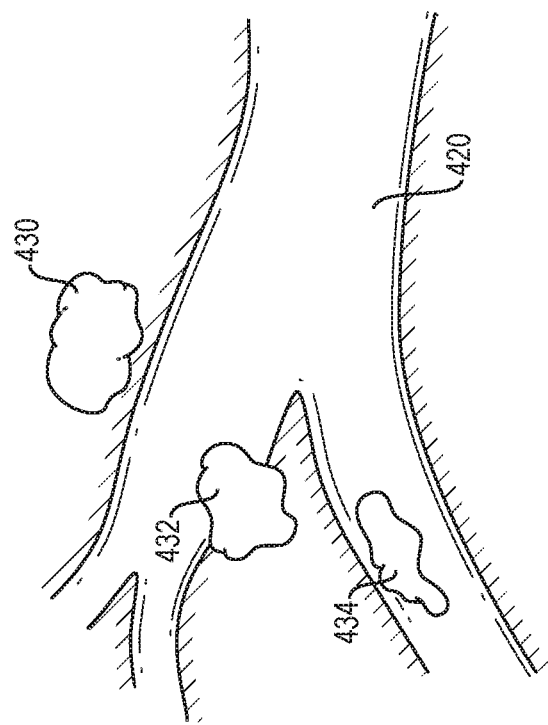
FIG. 11 is a schematic cross-sectional view of an airway or body lumen and three types of nodules.

FIG. 11 illustrates an airway 420 having a number of nodules therein. In general, nodules can be grouped into three or more types. For example, nodules located outside of an airway passage are generally referred to as extrinsic nodules 430. Nodules that span an airway wall 424 generally are referred to as mixed nodules 432. Nodules that are located within an airway 420 are generally referred to as intrinsic nodules 434. Each type of nodule presents its own challenges for access and treatment. Desirably, consistent and repeated access to any particular site proximate a nodule can be accomplished using one or more of the devices described herein. Advantageously, one or more of the devices described herein can be directly anchored proximate or at a region containing a site of interest such that the device will move with the site. For example, by anchoring to the tissue, airway, or other portion of the body that is adjacent to or that contains the region of interest, as the patient or recipient breaths or has other anatomical movement, one or more of the devices described herein will move with the region of interest. This provides distinct advantages over catheters, lumens and the like that provide a frame of reference to a location external to the body or the location of interest, for example. Such catheters, lumens and the like have a distal end that does not move with movement of the region of interest. For example, if the patient is breathing, relative movement between the lung tissue and the end of a catheter, bronchoscope or the like will occur with each breath. In some configurations, the devices or at least some portion of the devices described herein can function as fiducial markers. In some arrangements, more than two of the devices or more than two portions of one or more devices can be used to define a plane. Thus, the devices, or portions of the devices, can be used to locate nodules, or other sites of interest, visually or through other suitable techniques.

The present invention includes an anchoring feature(s) in a guide sheath to ensure that the guide sheath does not lose its location within the airway. The anchoring feature(s) can be activated manually by the user or triggered automatically by an instrument used in the working channel. The anchoring feature(s) will provide temporary, reversible anchoring for the distal tip of the guide sheath within the targeted airway.

As shown below, the present invention is an "end product" assembly of a guide sheath and anchoring system which can be used to temporarily maintain the position and orientation of the guide sheath tip. The internal diameter of the guide sheath allows instruments (needles, forceps, brushes, etc.) to pass through the sheath to reach the airway target. In one embodiment, the sheath contains additional working channels to allow control wires to transmit force from the proximal handle to the distal tip in order to engage anchor prongs. These wired prongs could be made of nitinol wire in either the superelastic or shape memory condition, or could be pre-formed from spring steel. There could be a number of wires spaced around the central working channel in various arrays of shapes.

Figure 12:
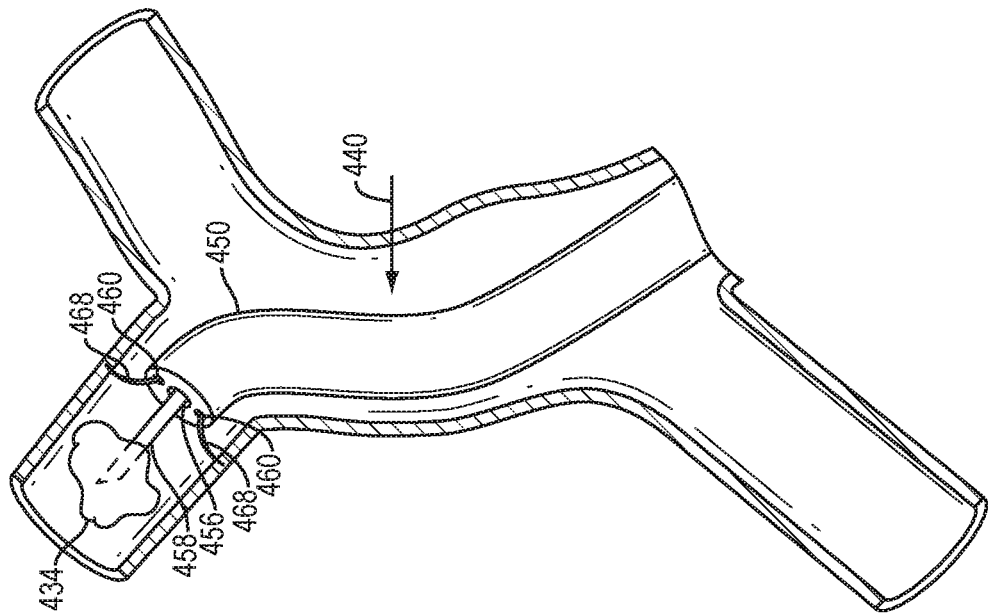
FIG. 12 is a side view of a distal end of a wire-based nodule access device in a first configuration deployed within an airway or other body lumen.

FIG. 12 illustrates an embodiment of an access device 440 that can, in some embodiments, span one or more generations of the bronchial tree. The access device 440 includes a proximal end (not shown) and a distal end. In some embodiments, the access device 440 includes a channel body portion 450. In some embodiments, a portion or all of the channel body portion 450 is substantially cylindrical or may have a polygonal cross-section. In some embodiments, the channel body portion 450 can be constructed of a PTFE-lined braid of reinforced PEBAX™ or some other suitable material.

In one embodiment, the channel body portion 450 includes a proximal end and a distal end. The channel body portion 450 includes an interior working channel 456. In some embodiments, the interior working channel 456 extends from the proximal end to the distal end. In some embodiments, the diameter of the working channel 456 is greater than about 1 mm and/or less than about 5 mm. In some embodiments, the diameter of the working channel 456 is approximately 2 mm. In some embodiments, when the channel body portion 450 is inserted into a body lumen, the proximal end remains exterior to the body.

In some embodiments, the access device 440 can include one or more anchor channels 460 that slidably receive anchors 468. The one or more anchor channels 460 extend from the proximal to the distal end of the channel body portion 450. The anchors 468 include a tissue piercing distal end and a proximal end accessible by an operator at the proximal end of the channel body portion 450. The anchors 468 may include pads, such as the pads 149 shown in FIG. 8D.

In one embodiment, the operator inserts the channel body portion 450 into a body lumen with the anchors 468 retracted within their respective anchor channels 460. The channel body portion 450 is advanced until the distal end of the channel body portion 450 reaches a desired location. Once the channel body portion 450 has reached the desired location, the operator advances the anchors 468, individually or simultaneously. As the anchors 468 exit the distal end of the channel body portion 450, the anchors 468 expand away from a longitudinal axis of the channel body portion 450. The anchors 468 are advanced until the tissue piercing tips penetrate walls of the lumen. After the anchors 468 are secured to the lumen walls, the proximal ends of the anchors 468 may be secured to the channel body portion 450, such as a handle device (not shown) at the proximal end. The anchors 468 keep the channel body portion 450 in place within the body lumen, thus allowing the operator to pass various medical devices (e.g., a needle 458) through the working channel 456 in order to interact with targets (e.g., nodules 430-434) at or near the distal end of the channel body portion 450.

In some embodiments, the body portion 450 of the access device 440 can be constructed of a stainless steel or nitinol hypotube or some other resilient material. The body portion 450 of the access device 440 can be cut using a laser, photochemical mill, water jet or other suitable process. In some configurations, the body portion 450, or a segment thereof can be cut in a braided pattern, a jigsaw pattern, a stop cut pattern and/or a serpentine pattern. Cutting the body portion 450 can increase the flexibility of the access device 440 and allow the access device 440 to more easily navigate tortuous airways or other body lumens. In some embodiments, the proximal end of the body portion 450 is cut to have increased flexibility. In some embodiments, cuts in the body portion 450 can be sealed with heat shrink protect the interior of the working channel 456. In some embodiments, PTFE, PEBAX™, or some other suitable material can be used to coat the interior of the working channel 456 and/or the exterior of the body portion 450. In some configurations, the body portion 450 is not cut.

In some embodiments, the access device 440 is deployed at a site of interest (e.g., a nodule) using a bronchoscope of other delivery device (e.g., an endoscope or delivery catheter). The access device 440 can be stored in a working channel or other lumen of a delivery device before deployment. In some embodiments, the access device 440 is configured to radially compress into the working channel or other lumen of a delivery device.

The access device 440 can navigate to the site of interest using a visualization device, such as, for example, an ultrasound probe or scope. The visualization device is included in the scope (e.g., fiber optic device) or can be sized and shaped to fit within the working channel or other lumen in which the access device 440 is stored prior to deployment. In some embodiments, the visualization device is sized and shaped to fit within (e.g., able to pass through) the access device 440 when the access device 440 is contained within the lumen of the delivery device. The access device 440 and/or lumen can be filled with a gel or other fluid to facilitate measuring continuity of the visualization device (e.g., ultrasound continuity of an ultrasonic probe).

The visualization device can be used to identify the specific location (e.g., the radial and/or circumferential location with respect to the delivery device) of the site of interest (e.g., nodule) near which the access device 440 is to be deployed. In some embodiments, the visualization device is configured to detect surface and/or structural features (e.g., echogenically unique features) of the access device 440. Such echogenically unique surface and/or structural features could include features that have different echogenicity from the portions of the access device 440 adjacent to or surrounding the features. In some such embodiments, the visualization device (e.g., ultrasound probe) can be used to detect the rotational orientation of the one or more anchors 468 (or other features such as, for example, cut patterns, side ports) of the access device 440. The access device 440 can be rotated within the lumen of the delivery device to rotationally align the relevant feature (e.g., the anchors 468, cut patterns, side ports) to a desired rotational position. For example, the anchor 468 can be aligned on the circumferentially opposite side of the lumen into which the access device 440 is deployed from the site of interest (e.g., a nodule).

Figure 13:
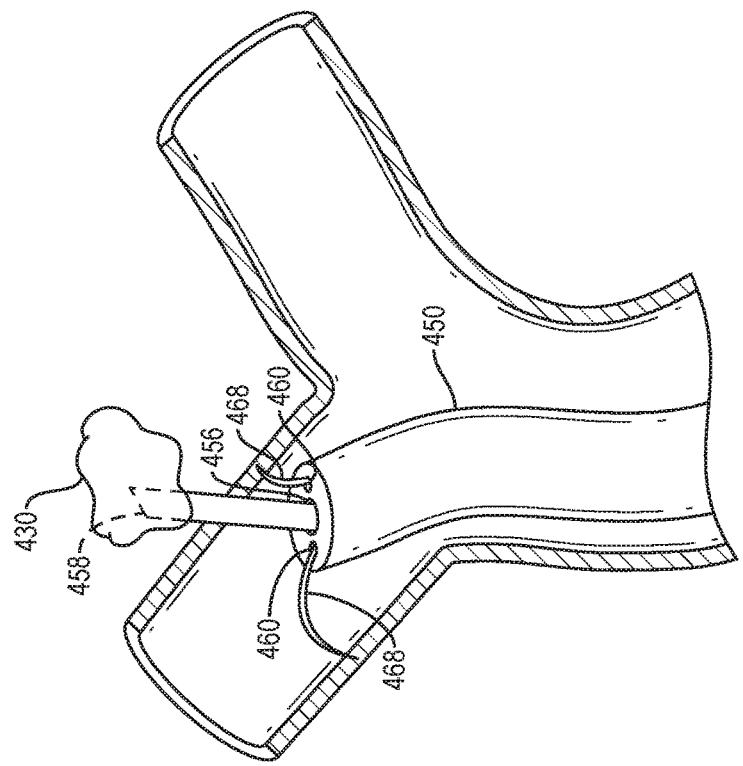
FIG. 13 is a side view of the distal end of the wire-based nodule access device of FIG. 12 in a second configuration deployed within an airway or other body lumen.

In one embodiment, based on different deployments of the anchor 468, the distal end of the access device 440 can be directed toward the site of interest. FIG. 13 illustrates the access device 440 with a normal vector of its distal face skewed at an angle away from a longitudinal axis of the lumen in which the access device 440 is located. In order for the access device 440 to maintain this skewed orientation, at least a first one of the anchors 468 is deployed at a shorter length than a second one of the anchors 468. The access device 440 may also be skewed based on the location where the ends of the anchors 468 make contact with the wall of the lumen. For example, a first one of the anchors 468 makes contact with the lumen wall at a location more proximal than other anchors 468. A combination of the methods described above may be used for altering the orientation of the distal end of the access device 440.

Figure 14:
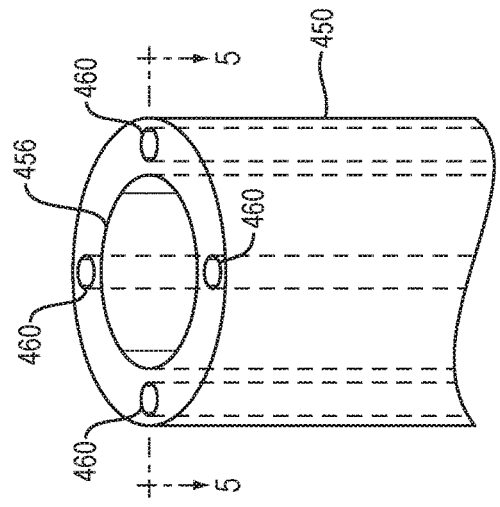
FIG. 14 is a perspective x-ray view of a distal end of a wire-based nodule access device formed in accordance with an embodiment of the present invention.

FIG. 14 illustrates a perspective x-ray view of a distal end of the access device 440. In this embodiment, the access device 440 includes the main center working channel 456 and four anchor channels 460.

Figure 15:
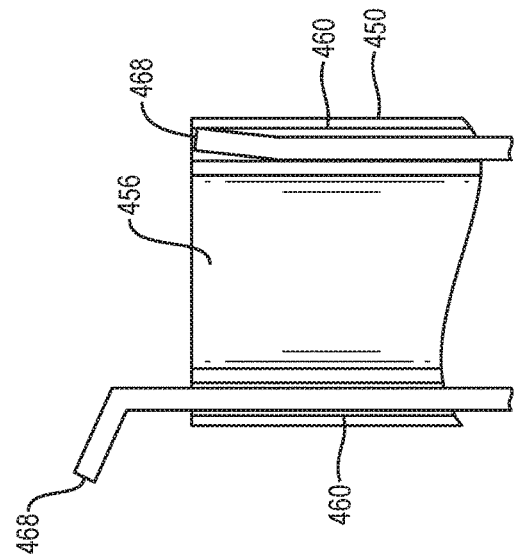
FIG. 15 is a cross-sectional view of a distal end of a wire-based nodule access device formed in accordance with an embodiment of the present invention.

As shown in FIG. 15, the anchors 468 are slidable within the anchor channels 460 to achieve various exposed or non-exposed positions. The anchors 468 may be mostly straight when they are within the anchor channels 460, but could deflect outward when deployed for making contact with tissue. The outward deflection may be achieved through a shape setting process used on the anchors 468 which is made of a shape set material or the anchors 468 may be configured in a preloaded shape.

Figure 16:
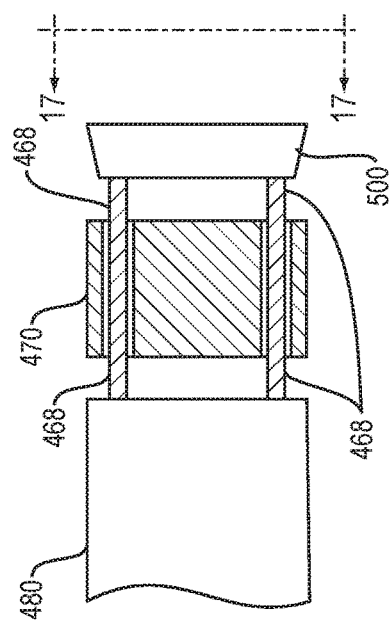
FIG. 16 is a cross-sectional view of a proximal end of a wire-based nodule access device formed in accordance with an embodiment of the present invention.

FIG. 16 shows a side cross-sectional view of a proximal end (i.e., handles) of the access device 440. The proximal end of the access device 440 is located outside of the patient when in use. In one embodiment, the proximal end of the access device 440 includes an anchor handle actuator 500, an anchor handle base 470 and a main handle 480. The anchor handle actuator 500 is attached to the proximal ends of one or more of the anchors 468. The proximal ends of the anchors 468 may be attached via adhesive or fasteners or friction fitted into cavities within the anchor handle actuator 500. The anchor handle actuator 500 keeps the anchors 468 from rotating within their respective anchor channel 460. Other methods of connecting the anchors 468 to the anchor handle actuator 500 may be used. A user controls positioning of the distal end of the access device 440 based on how they manipulate the anchor handle actuator 500. Movement of the anchor handle actuator 500 toward either the body portion 450 of the access device 440 or a handle component (not shown) of the access device 440 results in the anchors 468 moving distally eventually protruding from the distal end of the body portion 450.

In one embodiment, the anchor handle base 470 connects to a proximal end of the anchor handle actuator 500 via a Luer fitting or comparable connecting device(s). The anchor handle base 470 includes a lumen for each of the shafts of the anchors 468. The lumen in the anchor handle base 470 allow the anchors 468 to move longitudinally. In one embodiment, the anchor handle base 470 is not included.

Figure 17:
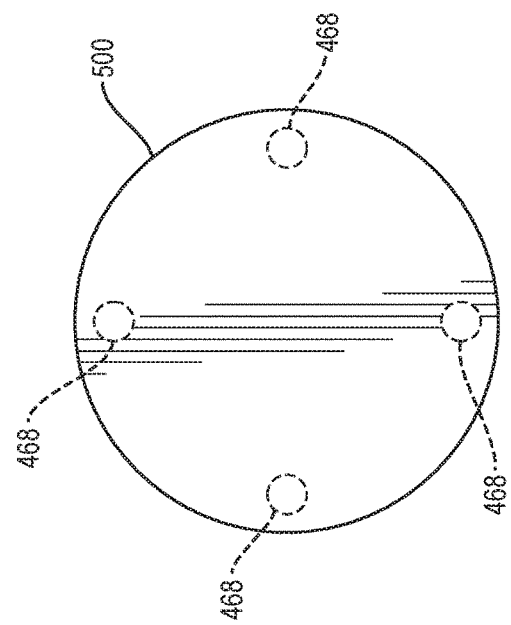
FIG. 17 is an end view of the proximal end of the wire-based nodule access device of FIG. 16.

In one embodiment, the proximal end of the anchors 468 are pivotally attached to the anchor handle actuator 500. This configuration allows one to be able to push one or more of the anchors 468 out of the distal end of the access device 440 without significantly changing the position of the other anchors 468. This allow one to manipulate orientation of the distal end of the access device 440, like that shown in FIG. 13, based on length of anchors exposed and/or where/when to deploy an anchor 468. FIG. 17 shows a proximal face of the anchor handle actuator 500 that is connected to the proximal ends of four anchors 468. The proximal ends of the anchors 468 are attached to the anchor handle actuator 500 such that the anchors 468 are unable to significantly rotate within the anchor channels 460. This configuration keys the anchors 468 so that they deploy consistently at the distal end of the device.

In one embodiment, the anchor handle actuator 500 includes multiple, separately controllable components. Each of the separately controllable components is connected to one of the anchors 468. This allows a user to deploy one of the anchors 468 without affecting position of the other anchors 468.

Figure 18:
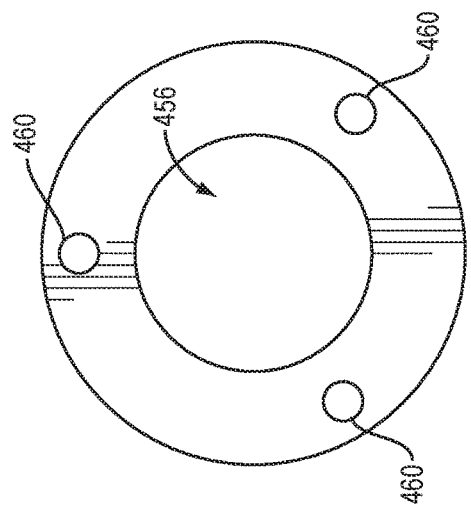
FIG. 18 is an end view of a distal surface of a wire-based nodule access device formed in accordance with an embodiment of the present invention.
Figure 19:
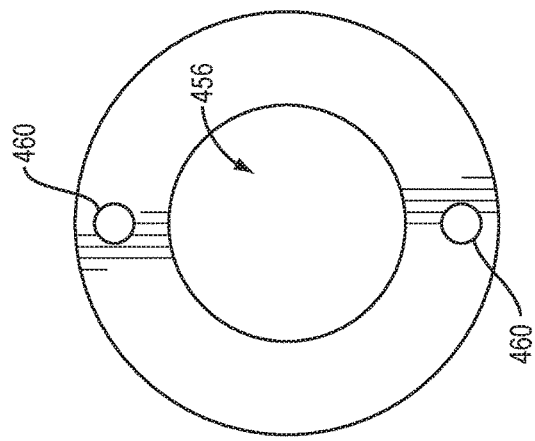
FIG. 19 is an end view of a distal surface of a wire-based nodule access device formed in accordance with an embodiment of the present invention.

FIG. 18 illustrates an anchor device that includes three anchor channels 460 and FIG. 19 illustrates an anchor device that includes two anchor channels 460.

EMBODIMENTS

A. A device for providing access to a nodule, lesion, or pathological area in a lung or other body organ or lumen, the device comprising: a sheath portion, the sheath portion having a proximal end and a distal end, the sheath portion comprising: a primary lumen that extends from the proximal end to the distal end; and a plurality of secondary lumens that extend from the proximal end to the distal end; and a plurality of stabilization wires, wherein at least one of the stabilization wires is configured to be slidably received within one of the secondary lumens, wherein the length of the stabilization wires is greater than the length of the secondary lumens.

B. The device of A, wherein the primary lumen comprises a first interior dimension, wherein the at least one of the secondary lumen comprises a second interior dimension, wherein the first interior dimension is larger than the second interior dimension.

C. The device of A or B, wherein the primary and secondary lumens include central longitudinal axes, wherein the central longitudinal axes of the second lumens are located further from a central longitudinal axis of the sheath portion than the central longitudinal axis of the primary lumen.

D. The device of any of A-C, further comprising a stabilization wire control device configured to allow a user to control deployment of the one or more of the stabilization wires at the distal end of the sheath portion.

E. The device of D, wherein the stabilization wire control device comprises a handle portion configured to flexibly attach to proximal ends of the stabilization wires.

F. The device of E, wherein the handle portion is configured to allow independent deployment of one or more of the stabilization wires.

G. The device of any of A-F, wherein at least one of the stabilization wires is keyed to a predefined orientation within a respective one of the second lumens.

H. The device of any of A-G, wherein the stabilization wires are configured to deflect away from a center axis of the sheath portion.

I. The device of any of A-H, wherein at least a portion of one or more of the stabilization wires comprises a shape memory material.

J. The device of any of A-I, wherein one or more of the stabilization wires comprises a piercing tip.

K. A method comprising: navigating a delivery device to a desired location with a lumen of a body; deploying a plurality of stabilization wires from a plurality of channels of the delivery device; attaching the stabilization wires to tissue proximate a target nodule; securing the stabilization wires relative to the delivery device; passing a treatment or diagnosis instrument through a central working channel of the delivery device; and treating or collecting a sample from the target nodule.

L. The method of K, further comprising: unsecuring the stabilization wires from the delivery device; detaching the stabilization wires from the tissue proximate the target nodule; and returning the plurality of stabilization wires to the plurality of channels of the delivery device.

M. The method of any of K or L, wherein the central working channel comprises a first interior dimension, wherein the at least one of the plurality of channels comprises a second interior dimension, wherein the first interior dimension is larger than the second interior dimension.

N. The method of any of K-M, wherein the central working channel and the plurality of channels include central longitudinal axes, wherein the central longitudinal axes of the plurality of channels are located further from a center axis of the delivery device than the central longitudinal axis of the central working channel.

O. The method of any of K-N, wherein deploying the stabilization wires comprises activating a stabilization wire control device configured to allow a user to control deployment of the one or more of the stabilization wires at a distal end of the delivery device.

P. The method of O, wherein the stabilization wire control device comprises a handle portion configured to flexibly attach to proximal ends of the stabilization wires.

Q. The method of P, wherein the handle portion is configured to allow independent deployment of two or more of the stabilization wires.

R. The method of any of K-Q, wherein at least one of the stabilization wires has a keyed relationship with a respective one of the plurality of channels.

S. The method of any of L-R, wherein attaching the stabilization wires comprises automatically deflecting one or more of the stabilization wires away from a center axis of the delivery device.

T. The method of any of K-S, wherein one or more of the stabilization wires comprises a shape memory material.

U. The device of A-C, wherein the central longitudinal axis of the primary lumen is collocated with the central longitudinal axis of the sheath portion.

Components of some or all of the devices described herein can be constructed of biocompatible materials in order to facilitate long term and/or permanent deployment of the device within the body. For example, components can be lined with silver of some other antimicrobial lining to reduce the likelihood that biological material will be deposited on or in the device. In some embodiments, components of the devices can be coated with or constructed of bioabsorbable material. In some embodiments, components of the devices can be coated with porous Teflon to encourage tissue ingrowth into the device.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

What is claimed is:
1. A method comprising:
navigating a delivery device to a desired location with a lumen of a body;
deploying a plurality of stabilization elements, from a distal end of the delivery device, into contact with tissue proximate a target nodule, wherein a first stabilization element of the plurality of stabilization ele- ments is deployable independently from a second stabilization element of the plurality of stabilization elements;

passing a treatment or diagnosis instrument through a central working channel of the delivery device while each of the first stabilization element and the second stabilization element are in contact with the tissue; and treating or collecting a sample from the target nodule.

2. The method of claim 1, further comprising:
returning the plurality of stabilization elements to the delivery device.

3. The method of claim 1, wherein the central working channel comprises a first interior dimension, wherein the deploying the stabilization elements is performed from a plurality of channels comprising a second interior dimension, wherein the first interior dimension is larger than the second interior dimension.

4. The method of claim 1, wherein the central working channel includes a central longitudinal axis, and
wherein deploying the stabilization elements occurs further from a center axis of the delivery device than the central longitudinal axis of the central working channel.

5. The method of claim 1, wherein deploying the stabilization elements comprises activating a stabilization elements control device configured to allow a user to control deployment of the stabilization elements.

6. The method of claim 5, wherein the stabilization elements control device comprises a handle portion configured to flexibly attach to proximal ends of the stabilization elements.

7. The method of claim 6, wherein the handle portion is configured to allow independent deployment of the stabilization elements.

8. The method of claim 6, wherein the handle portion includes a normal vector and the stabilization elements control device includes a base section having a longitudinal axis, wherein when the handle portion is in a neutral position, the normal vector aligns with the longitudinal axis of the base section.

9. The method of claim 8, wherein when the handle portion is positioned relative to the base section with the normal vector having an angular divergence from the longitudinal axis of the base section, the center axis will be deflected by an amount comparable to the angular divergence of the normal vector of the handle portion.

10. The method of claim 1, wherein at least one of the stabilization elements has a keyed relationship with a respective one of a plurality of stabilization element channels.

* * * * *